United States Patent
Pilgeram et al.

(10) Patent No.: US 10,231,744 B2
(45) Date of Patent: Mar. 19, 2019

(54) FLEXIBLE ACL INSTRUMENTATION, KIT AND METHOD

(71) Applicant: Howmedica Osteonics Corp., Mahwah, NJ (US)

(72) Inventors: Kyle Craig Pilgeram, San Jose, CA (US); Ran Oren, Kibbutz Gaaton (IL); Eran Zakai, Misgav (IL); Elad Rash, Beit Lehem Haglilit (IL)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/591,581

(22) Filed: Jan. 7, 2015

(65) Prior Publication Data

US 2015/0127012 A1    May 7, 2015

Related U.S. Application Data

(63) Continuation of application No. 12/859,580, filed on Aug. 19, 2010, now Pat. No. 9,232,954.

(Continued)

(51) Int. Cl.
*A61B 17/17* (2006.01)
*A61B 17/16* (2006.01)

(52) U.S. Cl.
CPC ...... *A61B 17/1764* (2013.01); *A61B 17/1631* (2013.01); *A61B 17/1637* (2013.01);
(Continued)

(58) Field of Classification Search
CPC ..... A61B 17/14; A61B 17/17; A61B 17/1714; A61B 17/1631; A61B 17/1615; A61B 17/1637; A61B 17/1675; A61B 17/1764
(Continued)

(56) References Cited

U.S. PATENT DOCUMENTS

| 749,624 A | 1/1904 | McCullough |
|---|---|---|
| 1,308,798 A | 7/1919 | Masland |

(Continued)

FOREIGN PATENT DOCUMENTS

| CA | 2713309 A1 | 2/2011 |
|---|---|---|
| DE | 3131496 A1 | 2/1983 |

(Continued)

OTHER PUBLICATIONS

European Search Report, EP 10173568, dated Nov. 30, 2010.
(Continued)

*Primary Examiner* — Zade Coley
*Assistant Examiner* — Jessica Weiss
(74) *Attorney, Agent, or Firm* — Lerner, David, Littenberg, Krumholz & Mentlik, LLP

(57) ABSTRACT

In a first embodiment, the present invention includes an instrumentation system for preparing a bone for soft tissue repair, the instrumentation system including a flexible drill pin capable of bending along a curved path; an aimer capable of engaging the flexible pin to bend the flexible pin; and a flexible reamer having a flexible portion along at least a portion of its length, the flexible portion comprising a plurality of laser cuts. In an alternate embodiment, the present invention may also include a method for preparing a bone tunnel in a femur adjacent a knee joint, the method including introducing a flexible drill pin into the knee joint; guiding the flexible drill pin towards a surface of the femur with an instrument introduced into the knee joint; drilling the flexible drill pin into the femur; removing the instrument from the knee joint; introducing a cannulated flexible reamer into the knee joint by placing the flexible pin within the cannulation of the flexible reamer; and reaming the bone tunnel in the femur along the path of the flexible pin.

21 Claims, 24 Drawing Sheets

Related U.S. Application Data

(60) Provisional application No. 61/358,502, filed on Jun. 25, 2010, provisional application No. 61/343,482, filed on Apr. 29, 2010.

(52) U.S. Cl.
CPC ...... *A61B 17/1675* (2013.01); *A61B 17/1714* (2013.01); *A61B 17/1615* (2013.01)

(58) Field of Classification Search
USPC .............................. 606/96–98, 80–85, 102
See application file for complete search history.

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,250,434 A | 7/1941 | Dugaw |
| 2,267,925 A | 12/1941 | Johnston |
| 2,382,019 A | 8/1945 | Miller |
| 2,461,947 A | 2/1949 | Weber |
| 2,494,229 A | 1/1950 | Collison |
| 2,515,365 A | 7/1950 | Zublin |
| 2,547,571 A | 4/1951 | Ettinger |
| 2,773,672 A | 12/1956 | Holmes et al. |
| 2,808,632 A | 10/1957 | Cline |
| 2,833,284 A | 5/1958 | Springer |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isberner |
| 3,580,256 A | 5/1971 | Wilkinson et al. |
| 3,596,342 A * | 8/1971 | Willfurth ............... E04F 21/00 29/275 |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 3,981,051 A | 9/1976 | Brumlik |
| 4,212,569 A | 7/1980 | Andersson et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A | 3/1987 | Trott |
| 4,706,659 A | 11/1987 | Matthews et al. |
| 4,728,231 A | 3/1988 | Kunimori et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,811,736 A | 3/1989 | Griggs et al. |
| 4,823,780 A | 4/1989 | Odensten et al. |
| 4,842,451 A | 6/1989 | Dugger |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,250,051 A * | 10/1993 | Maryan ............... A61B 17/1746 606/100 |
| 5,259,846 A | 11/1993 | Granger et al. |
| 5,269,785 A | 12/1993 | Bonutti |
| 5,269,809 A | 12/1993 | Hayhurst et al. |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,320,635 A | 6/1994 | Smith |
| 5,322,505 A | 6/1994 | Krause et al. |
| 5,324,308 A | 6/1994 | Pierce |
| 5,330,468 A | 7/1994 | Burkhart |
| 5,342,376 A | 8/1994 | Ruff |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,824 A | 6/1995 | Akerfeldt et al. |
| 5,423,860 A | 6/1995 | Lizardi et al. |
| 5,437,630 A | 8/1995 | Daniel et al. |
| 5,437,675 A | 8/1995 | Wilson |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,758 A | 7/1996 | Uschold et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,548,862 A | 8/1996 | Curtis |
| 5,554,151 A | 9/1996 | Hinchliffe |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,617 A | 12/1996 | Houser |
| 5,584,695 A | 12/1996 | Lal Sachdeva et al. |

(56) References Cited

U.S. PATENT DOCUMENTS

| | | |
|---|---|---|
| 5,584,835 A | 12/1996 | Greenfield |
| 5,601,550 A * | 2/1997 | Esser .............. A61B 17/1739 |
| | | 606/54 |
| 5,601,557 A | 2/1997 | Hayhurst |
| 5,601,561 A | 2/1997 | Terry et al. |
| 5,603,716 A | 2/1997 | Morgan et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,929 A * | 7/1997 | Callaway ............ A61B 17/025 |
| | | 606/87 |
| 5,649,963 A | 7/1997 | McDevitt |
| 5,658,289 A | 8/1997 | Boucher et al. |
| 5,658,313 A | 8/1997 | Thal |
| 5,662,658 A | 9/1997 | Wenstrom, Jr. |
| 5,664,914 A | 9/1997 | Taniguchi |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,671,695 A | 9/1997 | Schroeder |
| 5,674,279 A | 10/1997 | Wright et al. |
| 5,681,315 A | 10/1997 | Szabo |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,660 A | 11/1997 | Kauker et al. |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,700,266 A | 12/1997 | Harryman, II |
| 5,702,397 A | 12/1997 | Goble et al. |
| 5,707,374 A | 1/1998 | Schmidt |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,530 A | 3/1998 | Popken |
| 5,725,541 A | 3/1998 | Anspach, III et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,788,699 A | 8/1998 | Bobst et al. |
| 5,797,918 A | 8/1998 | McGuire et al. |
| 5,810,825 A | 9/1998 | Huebner |
| 5,814,056 A | 9/1998 | Prosst et al. |
| 5,820,464 A | 10/1998 | Parlato |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,895,179 A | 4/1999 | Gschwend et al. |
| 5,897,574 A | 4/1999 | Bonutti |
| 5,906,626 A | 5/1999 | Carrillo |
| 5,908,423 A | 6/1999 | Kashuba et al. |
| 5,921,986 A | 7/1999 | Bonutti |
| 5,928,244 A | 7/1999 | Tovey et al. |
| 5,941,139 A | 8/1999 | Vodehnal |
| 5,941,883 A | 8/1999 | Sklar |
| 5,947,659 A | 9/1999 | Mays |
| 5,948,002 A | 9/1999 | Bonutti |
| 5,951,559 A | 9/1999 | Burkhart |
| 5,954,747 A | 9/1999 | Clark |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,030,406 A | 2/2000 | Davis et al. |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,083,244 A | 7/2000 | Lubbers et al. |
| 6,083,522 A | 7/2000 | Chu et al. |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,193,724 B1 * | 2/2001 | Chan .................. A61B 17/175 |
| | | 606/102 |
| 6,210,415 B1 * | 4/2001 | Bester .............................. 606/96 |
| 6,224,608 B1 | 5/2001 | Ciccolella et al. |
| 6,245,081 B1 | 6/2001 | Bowman et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,296,659 B1 | 10/2001 | Foerster |
| 6,306,138 B1 | 10/2001 | Clark et al. |
| 6,306,159 B1 | 10/2001 | Schwartz et al. |
| 6,312,438 B1 | 11/2001 | Adams |
| 6,343,482 B1 | 2/2002 | Endo et al. |
| 6,352,538 B2 | 3/2002 | McGuire et al. |
| 6,358,253 B1 | 3/2002 | Torrie et al. |
| 6,364,886 B1 | 4/2002 | Sklar |
| 6,383,188 B2 | 5/2002 | Kuslich et al. |
| 6,416,517 B2 | 7/2002 | Harder et al. |
| 6,419,678 B1 * | 7/2002 | Asfora .............. A61B 17/1757 |
| | | 606/96 |
| 6,419,684 B1 | 7/2002 | Heisler et al. |
| 6,431,801 B2 | 8/2002 | Vasudeva et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,474,425 B1 | 11/2002 | Truax et al. |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,494,272 B1 | 12/2002 | Eppink et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,592,590 B2 * | 7/2003 | Simon .................. A61B 17/921 |
| | | 173/90 |

(56) References Cited

U.S. PATENT DOCUMENTS

| | | |
|---|---|---|
| 6,599,310 B2 | 7/2003 | Leung et al. |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,730,092 B2 | 5/2004 | Songer |
| 6,740,090 B1 | 5/2004 | Cragg et al. |
| 6,743,239 B1 | 6/2004 | Kuehn et al. |
| 6,746,451 B2 | 6/2004 | Middleton et al. |
| 6,773,450 B2 | 8/2004 | Leung et al. |
| 6,780,188 B2 | 8/2004 | Clark et al. |
| 6,783,533 B2 | 8/2004 | Green et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,848,152 B2 | 2/2005 | Genova et al. |
| 6,863,672 B2 | 3/2005 | Reiley et al. |
| 6,874,978 B2 | 4/2005 | Gongola |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,984,241 B2 | 1/2006 | Lubbers et al. |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,029,490 B2 | 4/2006 | Grafton et al. |
| 7,041,107 B2 | 5/2006 | Pohjonen et al. |
| 7,048,754 B2 | 5/2006 | Martin et al. |
| 7,056,331 B2 | 6/2006 | Kaplan et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,225,512 B2 | 6/2007 | Genova et al. |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,285,124 B2 | 10/2007 | Foerster |
| 7,309,338 B2 | 12/2007 | Cragg |
| 7,326,215 B2 | 2/2008 | Myers et al. |
| 7,331,263 B2 | 2/2008 | Erickson et al. |
| 7,357,804 B2 * | 4/2008 | Binder et al. ............ 606/96 |
| 7,371,253 B2 | 5/2008 | Leung et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,624,487 B2 | 12/2009 | Trull et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,829 B2 | 12/2010 | Kaplan et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,235 B2 | 2/2011 | Ellis |
| 7,892,256 B2 | 2/2011 | Grafton et al. |
| 7,901,431 B2 | 3/2011 | Shurnas |
| 7,905,903 B2 | 3/2011 | Stone et al. |
| 7,905,904 B2 | 3/2011 | Stone et al. |
| 7,909,547 B2 | 3/2011 | Jordan et al. |
| 7,909,851 B2 | 3/2011 | Stone et al. |
| 7,913,365 B2 | 3/2011 | Genova et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,963,967 B1 | 6/2011 | Woods |
| 7,981,117 B2 | 7/2011 | Newton et al. |
| 7,981,140 B2 | 7/2011 | Burkhart |
| 7,993,369 B2 | 8/2011 | Dreyfuss |
| 7,996,967 B2 | 8/2011 | Genova et al. |
| 7,996,968 B2 | 8/2011 | Genova et al. |
| 8,002,733 B2 | 8/2011 | Kraft et al. |
| 8,011,072 B2 | 9/2011 | Genova et al. |
| 8,015,678 B2 | 9/2011 | Genova et al. |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,043,253 B2 | 10/2011 | Kraft et al. |
| 8,057,500 B2 | 11/2011 | Mitusina |
| 8,070,750 B2 | 12/2011 | Wenstrom, Jr. et al. |
| 8,083,770 B2 | 12/2011 | Ruff et al. |
| 8,088,130 B2 | 1/2012 | Kaiser et al. |
| 8,100,940 B2 | 1/2012 | Leung et al. |
| 8,109,700 B2 | 2/2012 | Jordan et al. |
| 8,114,088 B2 | 2/2012 | Miller |
| 8,118,834 B1 | 2/2012 | Goraltchouk et al. |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,216,273 B1 | 7/2012 | Goraltchouk et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,246,652 B2 | 8/2012 | Ruff |
| 8,267,959 B2 | 9/2012 | Fallman |
| 8,273,106 B2 | 9/2012 | Stone et al. |
| 8,287,539 B2 | 10/2012 | Nelson et al. |
| 8,287,541 B2 | 10/2012 | Nelson et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,312,942 B2 | 11/2012 | Ho et al. |
| 8,317,825 B2 | 11/2012 | Stone |
| 8,337,525 B2 | 12/2012 | Stone et al. |
| 8,343,187 B2 | 1/2013 | Lamson et al. |

(56) References Cited

U.S. PATENT DOCUMENTS

| | | |
|---|---|---|
| 8,361,113 B2 | 1/2013 | Stone et al. |
| 8,366,713 B2 | 2/2013 | Long et al. |
| 8,394,129 B2 | 3/2013 | Morgenstern Lopez et al. |
| 8,398,678 B2 | 3/2013 | Baker et al. |
| 8,409,253 B2 | 4/2013 | Stone et al. |
| 8,430,884 B2 | 4/2013 | Re |
| 8,439,976 B2 | 5/2013 | Albertorio et al. |
| 8,460,338 B2 | 6/2013 | Goraltchouk et al. |
| 8,460,379 B2 | 6/2013 | Albertorio et al. |
| 8,469,998 B2 | 6/2013 | Sojka et al. |
| 8,512,340 B2 | 8/2013 | Easley et al. |
| 8,518,087 B2 | 8/2013 | Lopez et al. |
| 8,556,911 B2 | 10/2013 | Mehta et al. |
| 8,562,645 B2 | 10/2013 | Stone et al. |
| 8,568,413 B2 | 10/2013 | Mazur et al. |
| 8,591,578 B2 | 11/2013 | Albertorio et al. |
| 8,597,333 B2 | 12/2013 | Morgenstern Lopez et al. |
| 8,623,051 B2 | 1/2014 | Bojarski et al. |
| 8,663,324 B2 | 3/2014 | Schmieding et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 9,072,530 B2 | 7/2015 | Mehta et al. |
| 9,237,895 B2 * | 1/2016 | McCarthy ............ A61B 17/1714 606/96 |
| 9,795,398 B2 * | 10/2017 | Steiner ............... A61B 17/1764 |
| 2001/0016746 A1 | 8/2001 | McGuire et al. |
| 2002/0019635 A1 | 2/2002 | Wenstrom et al. |
| 2002/0183758 A1 | 12/2002 | Middleton et al. |
| 2002/0188301 A1 | 12/2002 | Dallara et al. |
| 2003/0032961 A1 | 2/2003 | Pelo et al. |
| 2003/0093080 A1 * | 5/2003 | Brown .................. A61F 2/4657 606/102 |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0033362 A1 | 2/2005 | Grafton |
| 2005/0038427 A1 | 2/2005 | Perriello et al. |
| 2005/0070906 A1 | 3/2005 | Clark et al. |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203523 A1 | 9/2005 | Wenstrom et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2005/0261604 A1 | 11/2005 | Stephens et al. |
| 2005/0283156 A1 | 12/2005 | Schmieding et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0015110 A1 | 1/2006 | Pepper |
| 2006/0074434 A1 | 4/2006 | Wenstrom et al. |
| 2006/0079904 A1 | 4/2006 | Thal |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0185532 A1 | 8/2007 | Stone et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0276392 A1 | 11/2007 | Beyar et al. |
| 2007/0288023 A1 | 12/2007 | Pellegrino et al. |
| 2007/0288031 A1 | 12/2007 | Dreyfuss et al. |
| 2008/0004659 A1 | 1/2008 | Burkhart et al. |
| 2008/0009904 A1 | 1/2008 | Bourque et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0065114 A1 | 3/2008 | Stone et al. |
| 2008/0071282 A1 | 3/2008 | Assell et al. |
| 2008/0082127 A1 | 4/2008 | Stone et al. |
| 2008/0082128 A1 | 4/2008 | Stone |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140092 A1 | 6/2008 | Stone et al. |
| 2008/0140093 A1 | 6/2008 | Stone et al. |
| 2008/0140116 A1 | 6/2008 | Bonutti |
| 2008/0147063 A1 | 6/2008 | Cauldwell et al. |
| 2008/0147064 A1 | 6/2008 | Cauldwell et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1 | 11/2008 | Stone et al. |
| 2008/0275453 A1 | 11/2008 | Lafosse et al. |
| 2008/0306483 A1 | 12/2008 | Iannarone |
| 2008/0312689 A1 | 12/2008 | Denham et al. |
| 2008/0319478 A1 | 12/2008 | Foerster et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 * | 6/2009 | Homan ............ A61B 17/1714 606/80 |
| 2009/0160112 A1 | 6/2009 | Ostrovsky |

(56) References Cited

U.S. PATENT DOCUMENTS

| | | | |
|---|---|---|---|
| 2009/0163935 A1* | 6/2009 | McCarthy | A61B 17/1714 606/150 |
| 2009/0171359 A1 | 7/2009 | Sterrett | |
| 2009/0192468 A1 | 7/2009 | Stone | |
| 2009/0194446 A1 | 8/2009 | Miller et al. | |
| 2009/0198258 A1 | 8/2009 | Workman | |
| 2009/0216236 A1* | 8/2009 | Re | A61B 17/1714 606/88 |
| 2009/0216238 A1 | 8/2009 | Stark | |
| 2009/0216243 A1 | 8/2009 | Re | |
| 2009/0222013 A1 | 9/2009 | Graf et al. | |
| 2009/0234386 A1 | 9/2009 | Dean et al. | |
| 2009/0240104 A1 | 9/2009 | Ogdahl et al. | |
| 2009/0248029 A1 | 10/2009 | Paulos | |
| 2009/0306671 A1 | 12/2009 | McCormack et al. | |
| 2009/0306711 A1 | 12/2009 | Stone et al. | |
| 2009/0312763 A1 | 12/2009 | McCormack et al. | |
| 2009/0312776 A1 | 12/2009 | Kaiser et al. | |
| 2009/0312792 A1 | 12/2009 | Fallin et al. | |
| 2009/0312793 A1 | 12/2009 | Huxel et al. | |
| 2009/0318961 A1 | 12/2009 | Stone et al. | |
| 2009/0326538 A1 | 12/2009 | Sennett et al. | |
| 2010/0049196 A1 | 2/2010 | Re | |
| 2010/0049202 A1 | 2/2010 | Re | |
| 2010/0049203 A1 | 2/2010 | Re | |
| 2010/0057045 A1 | 3/2010 | Albritton, IV et al. | |
| 2010/0076440 A1 | 3/2010 | Pamichev et al. | |
| 2010/0082033 A1 | 4/2010 | Germain | |
| 2010/0087857 A1 | 4/2010 | Stone et al. | |
| 2010/0121332 A1 | 5/2010 | Crainich et al. | |
| 2010/0121333 A1 | 5/2010 | Crainich et al. | |
| 2010/0145384 A1 | 6/2010 | Stone et al. | |
| 2010/0152739 A1 | 6/2010 | Sidebotham et al. | |
| 2010/0160962 A1 | 6/2010 | Dreyfuss et al. | |
| 2010/0185238 A1 | 7/2010 | Cauldwell et al. | |
| 2010/0185283 A1 | 7/2010 | Baird et al. | |
| 2010/0191241 A1 | 7/2010 | McCormack et al. | |
| 2010/0211075 A1 | 8/2010 | Stone | |
| 2010/0241121 A1 | 9/2010 | Logan et al. | |
| 2010/0249786 A1 | 9/2010 | Schmieding et al. | |
| 2010/0262146 A1 | 10/2010 | Tulkis | |
| 2010/0268275 A1 | 10/2010 | Stone et al. | |
| 2010/0292731 A1 | 11/2010 | Gittings et al. | |
| 2010/0292732 A1 | 11/2010 | Hirotsuka et al. | |
| 2010/0292792 A1 | 11/2010 | Stone et al. | |
| 2010/0298878 A1 | 11/2010 | Leung et al. | |
| 2010/0298879 A1 | 11/2010 | Leung et al. | |
| 2010/0305709 A1 | 12/2010 | Metzger et al. | |
| 2010/0318122 A1 | 12/2010 | Leung et al. | |
| 2011/0009902 A1 | 1/2011 | Leung et al. | |
| 2011/0015674 A1 | 1/2011 | Howard et al. | |
| 2011/0015675 A1 | 1/2011 | Howard et al. | |
| 2011/0022083 A1 | 1/2011 | DiMatteo et al. | |
| 2011/0022084 A1 | 1/2011 | Sengun et al. | |
| 2011/0046625 A1 | 2/2011 | Boileau et al. | |
| 2011/0054526 A1 | 3/2011 | Stone et al. | |
| 2011/0087247 A1 | 4/2011 | Fung et al. | |
| 2011/0087280 A1 | 4/2011 | Albertorio | |
| 2011/0087284 A1 | 4/2011 | Stone et al. | |
| 2011/0093010 A1 | 4/2011 | Genova et al. | |
| 2011/0098727 A1 | 4/2011 | Kaiser et al. | |
| 2011/0106089 A1 | 5/2011 | Brunnett et al. | |
| 2011/0106153 A1 | 5/2011 | Stone et al. | |
| 2011/0125189 A1 | 5/2011 | Stoll, Jr. et al. | |
| 2011/0152927 A1 | 6/2011 | Deng et al. | |
| 2011/0160767 A1 | 6/2011 | Stone et al. | |
| 2011/0160768 A1 | 6/2011 | Stone et al. | |
| 2011/0166581 A1* | 7/2011 | Van Der Merwe | A61B 17/1764 606/96 |
| 2011/0184516 A1 | 7/2011 | Baird et al. | |
| 2011/0208194 A1 | 8/2011 | Steiner et al. | |
| 2011/0208239 A1 | 8/2011 | Stone et al. | |
| 2011/0208240 A1 | 8/2011 | Stone et al. | |
| 2011/0213416 A1 | 9/2011 | Kaiser | |
| 2011/0213417 A1 | 9/2011 | Foerster et al. | |
| 2011/0218538 A1 | 9/2011 | Sherman et al. | |
| 2011/0218625 A1 | 9/2011 | Berelsman et al. | |
| 2011/0224799 A1 | 9/2011 | Stone | |
| 2011/0251621 A1 | 10/2011 | Sluss et al. | |
| 2011/0264138 A1 | 10/2011 | Avelar et al. | |
| 2011/0264140 A1 | 10/2011 | Lizardi et al. | |
| 2011/0264141 A1 | 10/2011 | Denham et al. | |
| 2011/0270278 A1 | 11/2011 | Overes et al. | |
| 2011/0270293 A1 | 11/2011 | Malla et al. | |
| 2011/0270306 A1 | 11/2011 | Denham et al. | |
| 2011/0295279 A1 | 12/2011 | Stone et al. | |
| 2011/0301708 A1 | 12/2011 | Stone et al. | |
| 2011/0319896 A1 | 12/2011 | Papenfuss et al. | |
| 2012/0004672 A1 | 1/2012 | Giap et al. | |
| 2012/0041485 A1 | 2/2012 | Kaiser et al. | |
| 2012/0041486 A1 | 2/2012 | Stone et al. | |
| 2012/0046693 A1 | 2/2012 | Denham et al. | |
| 2012/0053630 A1 | 3/2012 | Denham et al. | |
| 2012/0053641 A1 | 3/2012 | Meridew | |
| 2012/0059417 A1 | 3/2012 | Norton et al. | |
| 2012/0059418 A1 | 3/2012 | Denham et al. | |
| 2012/0089193 A1 | 4/2012 | Stone et al. | |
| 2012/0095470 A1 | 4/2012 | Kaiser et al. | |
| 2012/0109142 A1 | 5/2012 | Dayan | |
| 2012/0109156 A1 | 5/2012 | Overes et al. | |
| 2012/0109194 A1 | 5/2012 | Miller et al. | |
| 2012/0116452 A1 | 5/2012 | Stone et al. | |
| 2012/0123474 A1 | 5/2012 | Zajac et al. | |
| 2012/0150203 A1 | 6/2012 | Brady et al. | |
| 2012/0150297 A1 | 6/2012 | Denham et al. | |
| 2012/0150301 A1 | 6/2012 | Gamache et al. | |
| 2012/0165866 A1 | 6/2012 | Kaiser et al. | |
| 2012/0165867 A1 | 6/2012 | Denham et al. | |
| 2012/0165938 A1 | 6/2012 | Denham et al. | |
| 2012/0172986 A1 | 7/2012 | Stone et al. | |
| 2012/0180291 A1 | 7/2012 | Oren et al. | |
| 2012/0197271 A1 | 8/2012 | Astorino et al. | |
| 2012/0203231 A1 | 8/2012 | Long et al. | |
| 2012/0203288 A1 | 8/2012 | Lange et al. | |
| 2012/0209325 A1 | 8/2012 | Gagliano et al. | |
| 2012/0245585 A1 | 9/2012 | Kaiser et al. | |
| 2012/0253355 A1 | 10/2012 | Murray et al. | |
| 2012/0265205 A1 | 10/2012 | Steiner et al. | |
| 2012/0290002 A1 | 11/2012 | Astorino | |
| 2012/0290004 A1 | 11/2012 | Lombardo et al. | |
| 2012/0290006 A1 | 11/2012 | Collins et al. | |
| 2012/0296345 A1 | 11/2012 | Wack et al. | |
| 2012/0296427 A1 | 11/2012 | Conner et al. | |
| 2012/0303046 A1 | 11/2012 | Stone et al. | |
| 2013/0012962 A1 | 1/2013 | Stone | |
| 2013/0018416 A1 | 1/2013 | Lombardo et al. | |
| 2013/0023928 A1 | 1/2013 | Dreyfuss | |
| 2013/0023929 A1 | 1/2013 | Sullivan et al. | |
| 2013/0023930 A1 | 1/2013 | Stone et al. | |
| 2013/0035698 A1 | 2/2013 | Stone et al. | |
| 2013/0046341 A1 | 2/2013 | Stone et al. | |
| 2013/0053897 A1 | 2/2013 | Brown et al. | |
| 2013/0072989 A1 | 3/2013 | Overes et al. | |
| 2013/0085568 A1 | 4/2013 | Smith et al. | |
| 2013/0096611 A1 | 4/2013 | Sullivan | |
| 2013/0096612 A1 | 4/2013 | Zajac et al. | |
| 2013/0110165 A1 | 5/2013 | Burkhart et al. | |
| 2013/0116730 A1 | 5/2013 | Denham et al. | |
| 2013/0131722 A1 | 5/2013 | Marchand et al. | |
| 2013/0158601 A1 | 6/2013 | Stone et al. | |
| 2013/0165972 A1 | 6/2013 | Sullivan | |
| 2013/0190818 A1 | 7/2013 | Norton | |
| 2013/0237997 A1 | 9/2013 | Arai et al. | |
| 2013/0238025 A1 | 9/2013 | Howard et al. | |
| 2013/0245700 A1 | 9/2013 | Choinski | |
| 2013/0268000 A1 | 10/2013 | Harner et al. | |
| 2013/0296931 A1 | 11/2013 | Sengun | |
| 2013/0317544 A1 | 11/2013 | Ferguson et al. | |
| 2013/0345749 A1 | 12/2013 | Sullivan et al. | |
| 2014/0058390 A1 | 2/2014 | Taylor et al. | |
| 2014/0107657 A1* | 4/2014 | Norton | A61B 17/1796 606/96 |
| 2014/0114312 A1 | 4/2014 | Krause | |

(56) References Cited

U.S. PATENT DOCUMENTS

| | | |
|---|---|---|
| 2014/0135835 A1 | 5/2014 | Stone et al. |
| 2014/0188163 A1 | 7/2014 | Sengun |
| 2014/0207138 A1 | 7/2014 | Justin |

FOREIGN PATENT DOCUMENTS

| | | | |
|---|---|---|---|
| DE | 8903079 U1 | 5/1989 | |
| DE | 4231101 A1 | 3/1994 | |
| DE | 4243715 A1 | 7/1994 | |
| DE | 19503504 A1 | 3/1996 | |
| DE | 202009007979 U1 | 8/2009 | |
| EP | 153831 A2 | 9/1985 | |
| EP | 253526 A1 | 1/1988 | |
| EP | 0440371 A1 | 8/1991 | |
| EP | 0611551 A1 | 8/1994 | |
| EP | 1155776 A2 | 11/2001 | |
| EP | 1174584 A2 | 1/2002 | |
| EP | 1369089 A2 | 12/2003 | |
| EP | 1398455 A2 | 3/2004 | |
| EP | 2286742 A1 | 2/2011 | |
| EP | 2544607 A1 | 1/2013 | |
| EP | 2548519 A2 | 1/2013 | |
| ES | 1069589 U | 4/2009 | |
| FR | 1166884 A | 11/1958 | |
| FR | 2606996 A1 | 5/1988 | |
| FR | 2676638 A1 | 11/1992 | |
| GB | 2093353 A | 9/1982 | |
| WO | 95011631 A1 | 5/1995 | |
| WO | 9628100 A1 | 9/1996 | |
| WO | 9704908 A1 | 2/1997 | |
| WO | 9722301 A1 | 6/1997 | |
| WO | 0024327 A2 | 5/2000 | |
| WO | 00/44291 A1 | 8/2000 | |
| WO | 0128457 A1 | 4/2001 | |
| WO | 0160268 A1 | 8/2001 | |
| WO | 03007861 A1 | 1/2003 | |
| WO | 03086221 A1 | 10/2003 | |
| WO | 2004092531 A2 | 10/2004 | |
| WO | 2007/010389 A1 | 1/2007 | |
| WO | 2008128075 A1 | 10/2008 | |
| WO | 2009105880 A1 | 9/2009 | |
| WO | WO 2010/029409 A1 * | 3/2010 | ......... A61B 17/1764 |
| WO | 2011112371 A1 | 9/2011 | |
| WO | 2012134999 A1 | 10/2012 | |
| WO | 2012158583 A1 | 11/2012 | |

OTHER PUBLICATIONS

BIOMET Sports Medicine: Micromax Flex Suture Anchor, (2008).
International Search Report PCT/US2010/042264, dated Sep. 30, 2010.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
HHS Tube, Fort Wayne Metals Research Products Corp., 2009.
Cole et al., American Journal of Sports Medicine, vol. XX, No. X, 2011.
Medtronic, The VISAO High-Speed Otologic Drill Catalog, 2007.
Insall et al., The Journal of Bone and Joint Surgery, vol. 49B, No. 2, pp. 211-228, May 1967.
Chen et al., European Cells and Materials, vol. 16, Supp. 4, p. 7, 2008.
U.S. Appl. No. 13/085,882, filed Apr. 13, 2011.
U.S. Appl. No. 13/368,730, filed Feb. 8, 2012.
Extended European Search Report for Application No. EP 12164104 dated Jul. 11. 2012.
Burkinshaw, U.S. Appl. No. 60/418,545, filed Oct. 15, 2002.
International Search Report and Written Opinion for Application No. PCT/US2012/024303 dated May 24, 2012.
CONMED: LINVATEC: Shoulder Restoration System Y-Knot 1.3mm All Suture Anchor, © 2011 Linvatec Corporation, a subsidiary of ConMed Corporation—CBR 3057 (4 pages).
U.S. Appl. No. 13/303,849, filed Nov. 23, 2011.
U.S. Appl. No. 13/588,586, filed Aug. 17, 2012.
U.S. Appl. No. 13/588,592, filed Aug. 17, 2012.
U.S. Appl. No. 13/783,804, filed Mar. 4, 2013.
U.S. Appl. No. 61/679,336, filed Aug. 3, 2012.
Perthes, German Surgery Periodical, vol. 85, Commermorative Publication, pp. 2-18, 1906.
Perthes, Ober Operationen bel habitueller Schulterluxaton, X, pp. 199-227, 85.
Sugaya et al., Journal of Bone and Joint Surgery, vol. 85-A, No. 5, pp. 878-884, May 2003.
Canadian Office Action for Application No. 2773849 dated Aug. 5, 2013.
Canadian Office Action for Application No. 2,812,775 dated Aug. 23, 2013.
U.S. Appl. No. 13/792,982, filed Mar. 11, 2013.
U.S. Appl. No. 13/799,773, filed Mar. 13, 2013.
U.S. Appl. No. 13/182,851, filed Jul. 14, 2011.
U.S. Appl. No. 13/070,692, filed Mar. 24, 2011.
U.S. Appl. No. 12/682,324, filed Sep. 7, 2010.
Stamboulis, et al., "Mechanical properties of biodegradable polymer sutures coated with bioactive glass", Journal of Materials Science: Materials in Medicine, vol. 13, 2002, pp. 843-848.
Bretca, et al., "Bioactivity of degradable polymer sutures coated with bioactive glass", Journal of Materials Science: Materials in Medicine, vol. 15, 2004, pp. 893-899.
Boccaccini, et al., "Composite Surgical Sutures with Bioactive Glass Coating", J Biomed Mater Res Part B: Appl Biomater 67B, pp. 618-626, 2003.
Canadian Office Action for Application No. 2768020 dated Jan. 21, 2014.
Australian Examination Report for Application No. 2013202699 dated Feb. 21, 2014.
Partial European Search Report for Application No. EP14151822 dated May 16, 2014.
Canadian Office Action for Application No. 2,811,838 dated May 22, 2014.
Extended European Search Report for Application No. EP14159656 dated Jun. 6, 2014.
International Search Report and Written Opinion for Application No. PCT/US2014/021231 dated Jun. 25, 2014.
European Search Report for Application No. 10173568.6 dated Feb. 9, 2015.

* cited by examiner

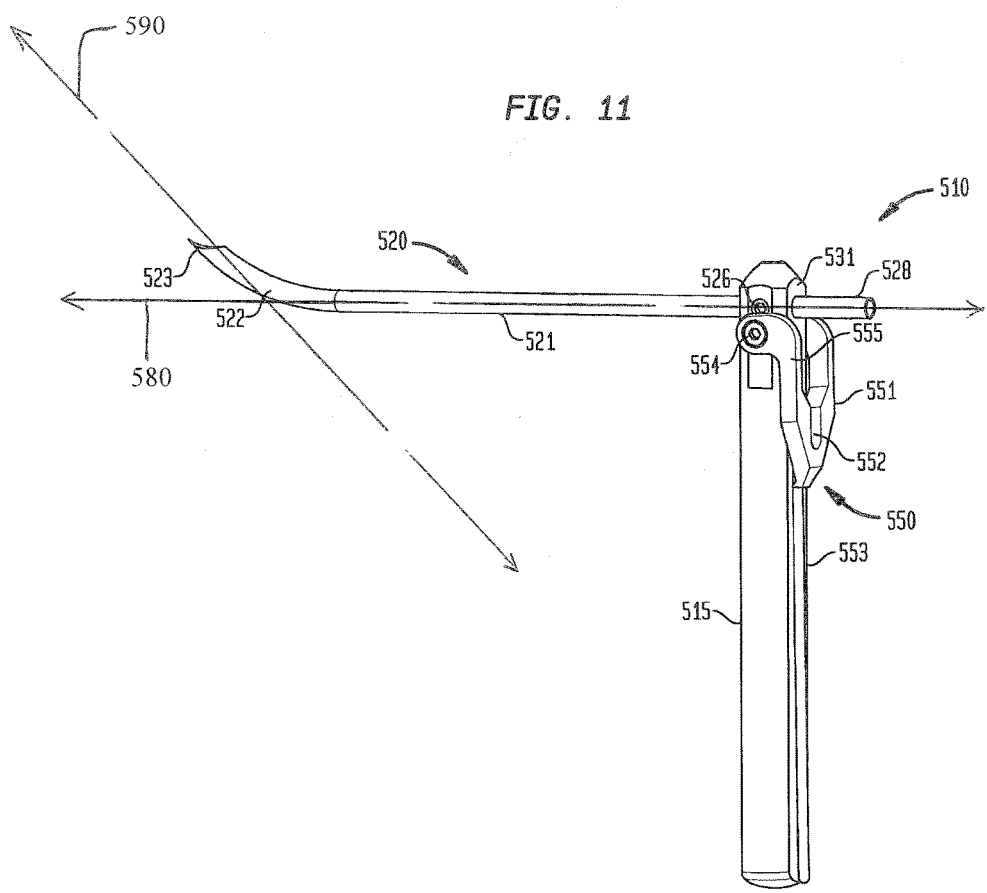

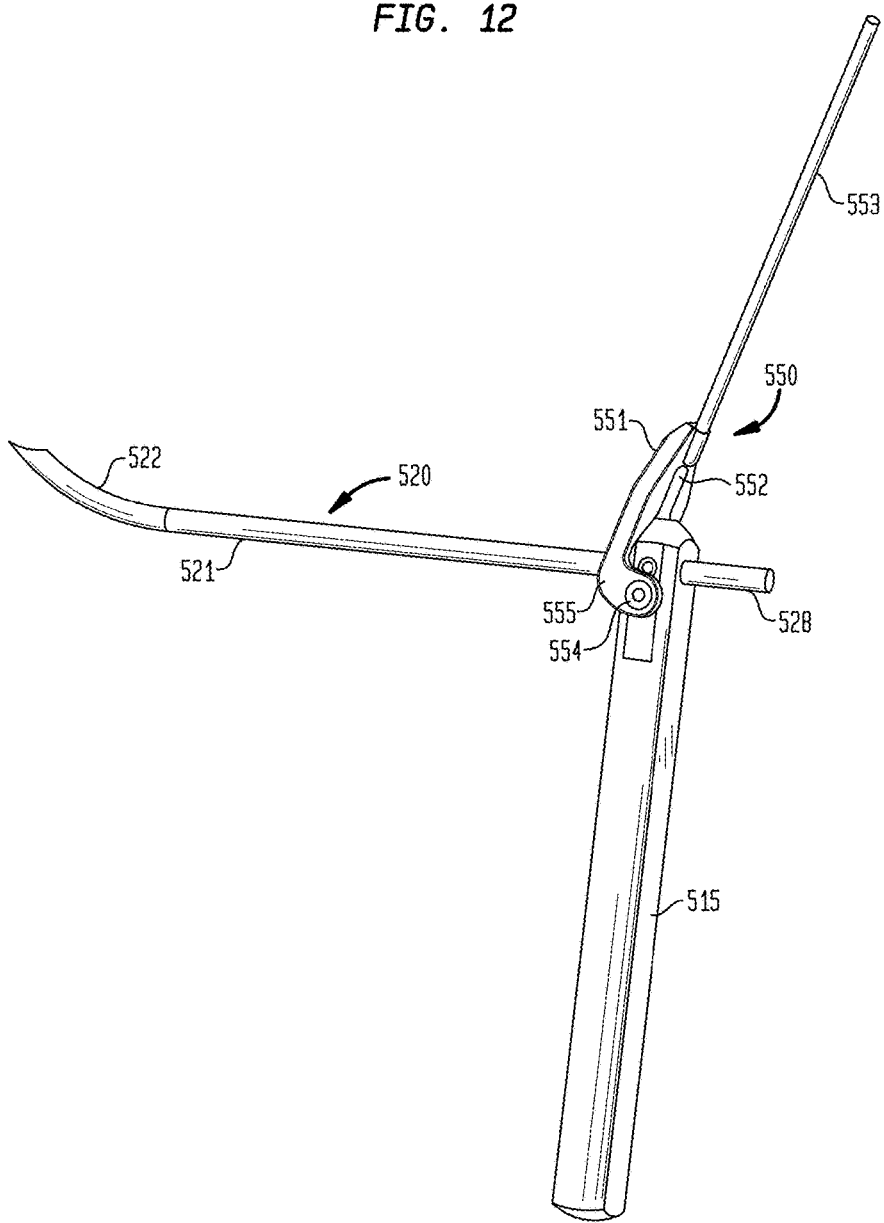

FLEXIBLE ACL INSTRUMENTATION, KIT AND METHOD

CROSS-REFERENCE TO RELATED APPLICATIONS

The present application is a continuation of U.S. patent application Ser. No. 12/859,580, filed on Aug. 19, 2010, which claims priority from U.S. Provisional Patent Application No. 61/343,482, filed on Apr. 29, 2010, and U.S. Provisional Patent Application No. 61/358,502, filed on Jun. 25, 2010, all of which are incorporated herein by reference.

BACKGROUND OF THE INVENTION

The present invention relates generally to instrumentation, kits and methods for repairing damage to soft tissue, including soft tissue such as tendons and ligaments, and particularly the anterior cruciate ligament (ACL) in the knee joint.

ACL injuries are often caused by a sudden force applied to the knee, and are a common form of injury in athletic activities. The injury occurs typically when the knee is bent or twisted in an awkward direction.

Current surgical repairs of ACL injuries may be arthroscopic or open and commonly include the formation of two bone tunnels, one in the tibia and one in the femur which serve as attachment points for a graft. Procedures for formation of the bone tunnels typically fall into two main categories. The first commonly uses a "trans-tibial" procedure in which an offset guide is placed through a tunnel drilled in the tibia. The offset guide positions a guide pin, also positioned through the tibial tunnel, towards the femur to form the femoral tunnel. However, this procedure often does not allow the surgeon to position the guide pin at the correct anatomical site of the native ACL on the femur. As a result, the rotational stability of the ACL replacement is reduced.

The second type of common surgical repair uses an "anterior-medial portal" procedure in which a similar offset guide is placed through a skin incision and into the joint. Since the guide is not within the tibial tunnel in this approach, the guide is less stable but has the freedom to be placed anywhere along the femoral notch. The length of the femoral tunnel is shorter than is usually desired, and the surgeon has to hyperflex the knee when inserting the drill pin. The hyperflexion has various drawbacks: the surgeon loses the visual reference to anatomic landmarks that are usually seen at a normal, ninety degree, flexion, and hyperflexion is difficult to do when using a leg holder, which is typically used in all repair procedures, or may be impossible due to a patient's build or anatomy. The surgeon can compromise tunnel integrity and thus fixation strength if the joint is not hyperflexed properly. However, if done properly, the native ACL attachment point may be accessed.

During such arthroscopic surgical procedures, particularly on a joint, such as a knee, a surgeon will force a clear liquid, such as saline or Ringer solution, into the joint to provide better viewing potential through an arthroscopic camera. The clear liquid forces blood and other fluids, suspended solids and debris from the joint. In order to maintain the joint volume free of these other substances, the clear liquid must be maintained at an elevated pressure, otherwise viewing ability is lost.

Typically in arthroscopic procedures, a surgeon will use a cannula, or the like, which provides an entryway for surgical tools into the joint, as well as, detrimentally, an exit for the clear liquid from the joint. Furthermore cannulated guide tools may be passed into the joint via a cannula or directly through surgical incisions. Such cannulated tools also provide a conduit for the clear liquid to exit the joint. When such instruments are used, the surgeon must increase the flow of clear fluid into the joint, using a fluid pump for example, to maintain the required elevated pressure. And in some instances, such a large amount of clear fluid is lost through the cannula or cannulated guide tool that maintaining the elevated pressure is not feasible. Moreover, the clear fluid may exit onto the surgeon's hands and even the floor, leading to dangerous safety conditions such as a slippery floor where the surgeon is working.

Thus, there is a need in ligament and tendon repair surgery for instrumentation and procedures which may be used, for example, for ACL repair surgery with the knee at various normal degrees of flexion, including ninety degree flexion and even at hyperflexion, if needed, which may be capable of aligning the drill pin to contact the femur at the native ACL attachment site, which may be simple and replicatable, which may be used in arthroscopic procedures in which a clear liquid is used within the surgical space, and which have other benefits over the existing instrumentation and procedures.

BRIEF SUMMARY OF THE INVENTION

The present invention may generally, in a first embodiment, include instrumentation for preparing the tibia and femur for ACL repair. The instrumentation may include any of a flexible pin, a femoral aimer, a curved guide tool and a flexible reamer. The use of these instruments may create tunnels through the tibia and femur for attachment of a graft (whether natural or artificial) which may serve as a replacement ACL. The instrumentation may further include other elements such as a power drill (for connection with at least one of the flexible pin and flexible reamer) and a starter awl (for forming a pilot divot at the insertion point on the tibia and/or femur).

In one embodiment, the present invention may include an instrumentation system for preparing a bone for soft tissue repair, the instrumentation system may include a flexible drill pin capable of bending along a curved path; an aimer capable of engaging the flexible pin to bend the flexible pin; and a flexible reamer having a flexible portion along at least a portion of its length, the flexible portion comprising a plurality of laser cuts.

The flexible drill pin may be composed of Nitinol, and may further include a distal portion and a proximal portion, wherein the distal portion includes a trocar tip and the proximal portion includes a suture connection. The aimer may further at least substantially surround a circumference of the flexible drill pin. The flexible portion of the flexible reamer may further include discrete, interlocking portions, and may also be cannulated along at least a portion of its length for placement of the flexible reamer over the flexible pin. The flexible portion may also be cannulated along at least a portion of its length for placement over at least the bent portion of the flexible pin. The flexible reamer may further include an asymmetric tip having at least one flute positioned off-axis relative to a longitudinal axis of the flexible reamer.

The instrumentation system may further include additional instrumentation such as a starter awl, suture and other instruments used in arthroscopic orthopedic surgery. The system may be used on a femur and an ACL, wherein the instrumentation system forms a tunnel in the femur extending from the knee joint.

In an alternate embodiment, the present invention may be a method for preparing a bone tunnel in a femur adjacent a knee joint, the method may include introducing a flexible drill pin into the knee joint; guiding the flexible drill pin towards a surface of the femur with an instrument introduced into the knee joint; drilling the flexible drill pin into the femur; removing the instrument from the knee joint; introducing a cannulated flexible reamer into the knee joint by placing the flexible pin within the cannulation of the flexible reamer; and reaming the bone tunnel in the femur along the path of the flexible pin.

The method may further include the step of the instrument guiding the flexible pin along a curved path towards the surface of the femur. The flexible drill pin may further be drilled through the femur and may exit out a lateral side of the femur. Additionally, the flexible drill pin may follow a curved path from introduction in the knee joint to the surface of the femur, and may follow a generally straight and substantially linear path from the surface of the femur, through the femur, and out the lateral side of the femur. The instrument may be a femoral aimer or a curved guide tool. The flexible reamer may further include a flexible portion along at least a portion of a length of the flexible reamer, the flexible portion comprising a plurality of laser cuts. The flexible portion of the flexible reamer may further include discrete, interlocking portions.

In this method, the flexible drill pin, instrument, and flexible reamer may also be introduced into the knee joint through an at least one portal. Alternatively, the flexible drill pin and flexible reamer may be introduced into the knee joint through a bone tunnel through a tibia, and the instrument may be introduced into the knee joint through a portal.

In another embodiment, the present invention may include instrumentation for preparing bone tunnels which may include a flexible pin, a femoral aimer, and a flexible reamer. A first embodiment of a flexible reamer may include a tip having at least one flute wherein the flute is positioned on the tip asymmetrically (i.e., off-axis relative to the longitudinal axis of the reamer). The tip may further include additional flutes which may be smaller in size than the first flute, thus maintaining an asymmetrical tip.

The present invention may also include various embodiments for methods of use of the instrumentation for bone tunnel preparation for ACL repair. These embodiments may be used when the knee is positioned at a "normal" flexion, for example, at ninety degrees, and a knee holder (as is known in the art) may also be used, if needed. Typically, the flexible pin is passed through the tibia and then through the knee joint and into the femur. An anterior-medial portal may also be formed, through which the femoral aimer passes through the skin and into the joint. The femoral aimer interacts with the flexible pin, as the pin passes through the joint, and may guide the pin to the proper location on the femur. In one example, the femoral aimer adjusts the trajectory of the pin such that the pin follows a curved path from the tibia to the femur.

A further embodiment of the methods of the present invention may include a method for preparing bone tunnels including the steps of placing a flexible pin through one of a portal or a bone tunnel, placing an aimer through the portal, contacting a distal portion of the pin with the aimer to alter the trajectory of the pin towards a desired position, pushing the pin through bone, placing a flexible reamer onto the pin and moving the reamer along the pin to create a second tunnel.

In one embodiment, the method of ACL repair may include forming a tibial tunnel in a knee joint, forming an anterior-medial portal in the knee joint, placing a flexible pin through the tibial tunnel and into the knee joint, placing a femoral aimer through the anterior-medial portal, contacting a distal portion of the pin with the aimer to alter the trajectory of the pin towards a position on the femur, drilling the pin through the femur, placing a flexible reamer onto the pin and moving the reamer along the pin passing through the tibial tunnel and reaming a femoral tunnel along a portion of the length of the pin within the femur, removing the reamer, connecting a suture and graft to a suture connector on a proximal end of the pin, pulling the pin proximally to pull the graft through the tibial tunnel and into the femoral tunnel, and securing the graft.

In a further embodiment, the method of ACL repair may include forming a tibial tunnel through a tibia. The tunnel may be directed in a proximal direction through the tibial plateau and may open into the knee joint. The tunnel may be formed using a drill. The drill may then be removed from the tibia and a flexible pin may be passed up through the tibia. The pin should be passed through the tibia until a distal portion extends into the knee joint. An anterior-medial portal may also be formed through the skin to allow access into the knee joint. A femoral aimer may be passed through the portal and positioned within the knee joint. As the distal portion of the pin enters the joint, the femoral aimer may interact with the pin to adjust the trajectory of the pin and guide it towards a desired location on the femur. Optionally, the desired location on the femur may be marked using a starter awl, or other instrument, to form a pilot divot. Once the pin is placed against the femur, the pin may be passed through the femur until it exits the femur, proximal to the knee joint, and through the adjacent skin. A flexible reamer (which may, for example, be cannulated) may then be positioned onto the pin such that the flexible reamer passes through the tibial tunnel and contacts the femur. The reamer may then be used to form a femoral tunnel to a specified depth. Leaving the pin in place, the reamer may then be removed from the femur and tibia. The pin may have a suture connector on its proximal portion (i.e., an eyelet or the like), through which a suture is passed which may contain a graft thereon. The pin is then pulled proximally, from where it exited the femur, to pull the suture and graft up through the tibial tunnel and into the femoral tunnel. The graft may then be secured.

In another embodiment, the method may include forming a tibial tunnel through the tibia. The tunnel may be directed in a proximal direction through the tibial plateau and may open into the knee joint. The tunnel may be formed using a drill. The drill may then be removed from the tibia and a flexible pin may be passed up through the tibia. The pin should be passed through the tibia until a distal portion extends into the knee joint. An anterior-medial portal may also be formed through the skin to allow access into the knee joint. A femoral aimer may be passed through the portal and positioned within the knee joint. As the distal portion of the pin enters the joint, the femoral aimer may interact with the pin to adjust the trajectory of the pin and guide it towards a desired location on the femur. Optionally, the desired location on the femur may be marked using a starter awl, or other instrument, to form a pilot divot. Once the pin is placed against the femur, the pin may be passed through the femur until it exits the femur, proximal to the knee joint, and through the adjacent skin. The pin may have a suture connector on its proximal portion (i.e., an eyelet or the like), through which a suture is passed. The pin is then pulled proximally, from where it exited the femur, to pull the suture up through the tibial tunnel and into the joint space. The suture and/or proximal portion of the pin may be grasped by an instrument through the anterior-medial portal, and the pin may then be pulled backwards through the portal. A flexible reamer (which may, for example, be cannulated) may then be positioned onto the pin such that the flexible reamer passes through the portal and contacts the femur. The reamer may then be used to form a femoral tunnel to a specified depth. Leaving the pin in place, the reamer may then be removed from the femur and the portal. A suture may be attached to the proximal portion of the pin. The pin may then be pulled, from its distal end, back up through the femoral tunnel, until the proximal end of the pin is visible within the knee joint. The pin may then be moved distally back through the tibial tunnel utilizing the suture or the suture connector, such that the suture and suture connector are outside the tibia. A suture, containing a graft, may be placed on the suture connector. The pin is then pulled proximally, from where it exits the femur, to pull the suture and graft up through the tibial tunnel and into the femoral tunnel. The graft may then be secured.

In yet another embodiment, the method may include passing a flexible pin through the tibia. The pin may be directed in a proximal direction through the tibial plateau and into the knee joint. An anterior-medial portal may also be formed through the skin to allow access into the knee joint. A femoral aimer may be passed through the portal and positioned within the knee joint. As the distal portion of the pin enters the joint, the femoral aimer may interact with the pin to adjust the trajectory of the pin and guide it towards a desired location on the femur. Optionally, the desired location on the femur may be marked using a starter awl, or other instrument, to form a pilot divot. Once the pin is placed against the femur, the pin may be passed through the femur until it exits the femur, proximal to the knee joint, and through the adjacent skin. A flexible reamer (which may, for example, be cannulated) may then be positioned onto the pin such that the flexible reamer drills through the tibia and the femur in a single continuous motion to form a tibial tunnel and a femoral tunnel. The reamer may form a femoral tunnel to a specified depth. Leaving the pin in place, the reamer may then be removed from the femur and tibia. The pin may have a suture connector on its proximal portion (i.e., an eyelet or the like), through which a suture is passed which may contain a graft thereon. The pin is then pulled proximally, from where it exited the femur, to pull the suture and graft up through the tibial tunnel and into the femoral tunnel. The graft may then be secured.

In another embodiment, the method may include forming a tibial tunnel through the tibia. The tunnel may be directed in a proximal direction through the tibial plateau and may open into the knee joint. The tunnel may be formed using a drill with a diameter which is narrower than the diameter of the final tibial tunnel, discussed below. The narrow-diameter drill may then be removed from the tibia and a flexible pin may be passed up through the tibia. The pin should be passed through the tibia until a distal portion extends into the knee joint. An anterior-medial portal may also be formed through the skin to allow access into the knee joint. A femoral aimer may be passed through the portal and positioned within the knee joint. As the distal portion of the pin enters the joint, the femoral aimer may interact with the pin to adjust the trajectory of the pin and guide it towards a desired location on the femur. Optionally, the desired location on the femur may be marked using a starter awl, or other instrument, to form a pilot divot. Once the pin is placed against the femur, the pin may be passed through the femur until it exits the femur, proximal to the knee joint, and through the adjacent skin. A flexible reamer (which may, for example, be cannulated), having a larger diameter than the narrow-diameter drill, may then be positioned onto the pin such that the flexible reamer expands the diameter of the tibial tunnel and contacts the femur. The reamer may then be used to form a femoral tunnel to a specified depth. Leaving the pin in place, the reamer may then be removed from the femur and tibia. The pin may have a suture connector on its proximal portion (i.e., an eyelet or the like), through which a suture is passed which may contain a graft thereon. The pin is then pulled proximally, from where it exited the femur, to pull the suture and graft up through the tibial tunnel and into the femoral tunnel. The graft may then be secured.

In yet another embodiment, the instrumentation may include a curved guide tool which may have a hollow curved guide, a handle, and an outrigger.

Additionally, the curved guide may have a bone engaging tip. Alternatively, the curved guide may have a flange, which may further be adapted to engage the surrounding anatomy adjacent to or on the bone.

The bone engaging tip may be any one of a single point, positioned anywhere on a distal end of the curved guide, or may include more than one point, wherein the points are positioned anywhere on the distal end of the curved guide.

The flange may have an offset from a longitudinal axis of the curved guide and may further have a shape adapted to engage a structure on hard or soft tissue at a surgical site. The offset may further be at any angle, such as between about 0 degrees and 90 degrees. The flange may further have a second offset, distal to the first offset. The second offset may be more than 0 degrees, and more specifically at least 20 degrees, and even more particularly about 45 degrees.

Additionally, the outrigger may swivel relative to the handle and curved guide. The outrigger may also include an extension having a longitudinal axis along its length. The handle, curved guide, and outrigger may all be positioned generally along a single plane. The curved guide may further be hollow along its length to allow passage of a pin, guidewire, or the like therethrough, for placement into the bone. In yet another embodiment, a curved guide tool may include a curved guide having a flange on a distal end and an outrigger. The flange may further be adapted to substantially mate with a portion of the anatomy at the surgical site. The outrigger may further be adapted to lay along outer tissue, for example, skin, outside of the surgical site but along the same plane as the curved guide. The curved guide tool may further include a handle.

The instrumentation may be used within a joint, such as a knee joint. Further, the instrumentation may be used on a femur bone to repair surrounding soft tissue. For example, the instrumentation may be used for ACL repair, such as attachment of an ACL to the femur, wherein the ACL is a natural ACL, ACL graft, ACL implant, tendon graft, bone-tendon-bone graft or the like.

The present invention also includes various embodiments for methods of use of the instrumentation for bone preparation for soft tissue repair, such as ACL repair. In one embodiment, the method may include forming an anterior-medial portal in soft tissue adjacent a knee joint; inserting a curved guide of a curved guide tool through the portal and into the joint; directing a distal tip of the curved guide towards the surface of a bone; engaging an outrigger with the outer surface of the skin of the body, the outrigger having a longitudinal axis extending along its length; and passing a pin through the curved guide and into the bone, wherein the pin passes through the bone and protrudes through the skin in a direction generally towards the axis of the outrigger.

The step of directing the distal tip of the curved guide towards the surface of the bone may further include engaging the bone with the distal tip of the curved guide wherein the distal tip is pointed. This step may alternatively include engaging anatomy, such as soft tissue, overlying the bone, with the distal tip of the curved guide wherein the distal tip is a flange. The flange may further be adapted to match the anatomy of the soft tissue. Either of the pointed tip or flange configurations may provide a surgeon with assurance that the curved guide is in proper placement for the ACL repair.

In yet another embodiment, the curved guide tool having the distal point may first be positioned at the surgical site. The distal point may then be used as an awl to mark the correct entry point for the pin. Then, this curved guide tool may be removed, and the curved guide tool having the flange may next be positioned at the surgical site. The curved guide tool having the flange may then be positioned on the anatomy and the pin passed through the curved guide into the bone.

The instrumentation may include a cannulated guide tool which may have a hollow guide, a handle, and a plug. The cannulated guide tool may further optionally include an outrigger. The cannulated guide may further be hollow along its length to allow passage of a pin, guidewire, or the like therethrough, for placement into the joint or bone.

In one embodiment, the plug may be a type of one-way valve. The plug may open to allow the passage of a pin, or the like, into the joint, but may close to prohibit the flow of fluid from the joint and out the cannulated guide. In one arrangement, the plug may include a dam which may pivot on an axis between an open position and a closed position. The plug may further include a manual activation which a surgeon may use to manually move the dam from an open position to a closed position.

In a further embodiment, the present invention may include a cannulated guide tool including a cannulated opening, a handle and a plug positioned within the cannulated opening. The plug may further include a dam and a pivot on which the dam rotates from a closed position, substantially blocking the cannulated opening, to an open position, substantially clear of the cannulated opening. The plug may further include a manual activation to manually pivot the dam between the open and closed positions. The plug may alternatively, in a different arrangement, include a spring bias to maintain the dam in one of an open or closed position. The plug may further include the dam having a tapered portion.

The present invention also includes various embodiments for methods of use of the instrumentation for bone preparation for soft tissue repair, such as ACL repair. In one embodiment, the method may include establishing a supply source of a clear fluid into a joint, such as a knee; forcing the clear fluid into the knee joint from the supply source; forming an anterior-medial portal in soft tissue adjacent the joint; inserting a cannulated guide of a cannulated guide tool through the portal and into the joint, the cannulated guide tool comprising a plug positioned in a closed position; directing a distal tip of the curved guide towards the surface of a bone; and passing a pin through the curved guide and into the bone, wherein the plug is pivoted to an open position upon entry of the pin into the cannulated guide. The method may further include removing the pin from the joint and cannulated guide, wherein the plug returns to the closed position.

Other variations of the instrumentation and methods disclosed herein relating to soft tissue repair, whether as to ACL or other soft tissues, are also within the scope of this invention.

BRIEF DESCRIPTION OF THE DRAWINGS

FIGS. 11 and 12 illustrate a first embodiment of a curved guide tool of the present invention in various configurations.

DETAILED DESCRIPTION

While the following instrumentation and surgical methods may be used to repair any suitable type of soft tissue—such as ligaments and tendons in a knee, hip, ankle, foot, shoulder, elbow, wrist, hand, spine, or any other area of anatomy—arthroscopic repairs of an ACL in a knee joint will be the exemplary focus of the disclosure below. In most of the below embodiments, the present invention forms a tibial bone tunnel and a femoral bone tunnel, each of which engages one end of an ACL replacement graft. The bone tunnels are intended to be positioned substantially at the location of the native ACL connection sites, though other locations may be used as desired or required based on the specific circumstances of a particular patient.

Figure 1A:
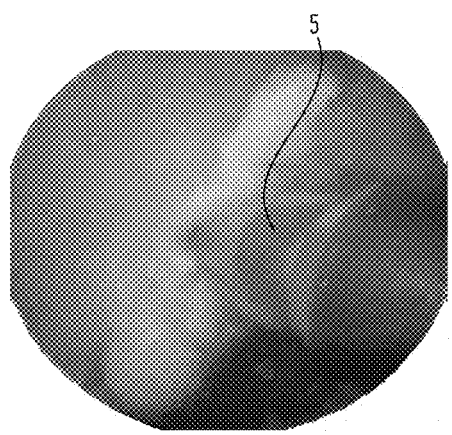
FIGS. 1A and 1B, illustrated as photographs, illustrate one embodiment of a starter awl.
Figure 1B:
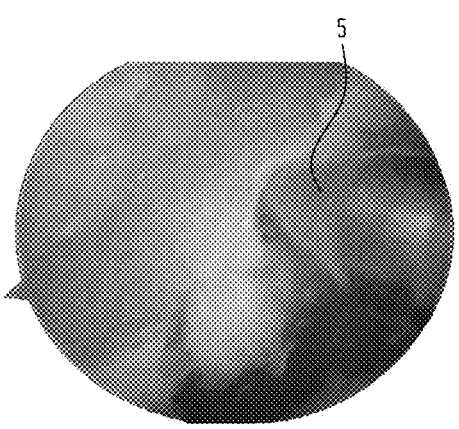

In a first embodiment, the instrumentation system may optionally include a starter awl 5 configured to create a pilot divot on the bone which will designate an anatomic insertion point. The awl, as illustrated in FIGS. 1A-B, may form a divot within which a flexible pin, or other instrument, may be positioned. In one example, the awl 5 may be used to form a pilot divot on a femur to designate the location of where the femur tunnel will be positioned.

Figure 2:
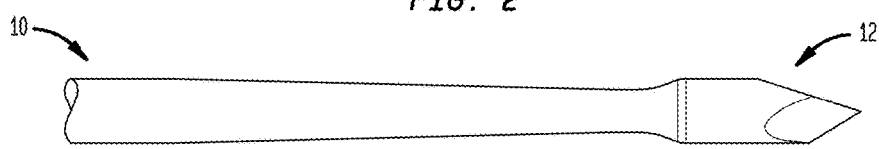
FIGS. 2, 3 and 4 illustrate various embodiments of distal tips of flexible pins, including examples of various dimensions of the pins thereon.
Figure 3:
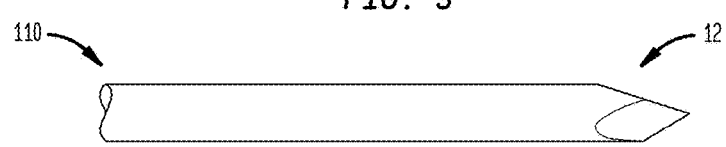
Figure 4:
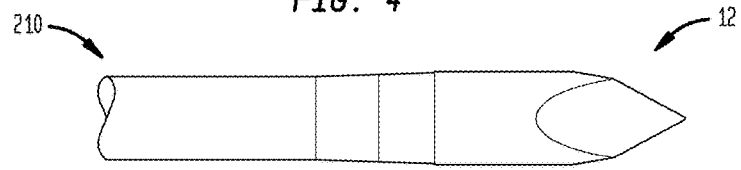

The instrumentation system may also include a flexible drill pin 10, 110, 210, various embodiments of which are illustrated in FIGS. 2-4. The pin includes a distal portion and a proximal portion (not shown). The distal portion 12 includes a trocar tip and may further include a tapered surface. The proximal portion may include a suture connection such as an eyelet, or the like, for connection of a suture to the pin. FIG. 3 illustrates one embodiment of a simple distal portion of a pin which includes a trocar tip. FIGS. 2 and 4 illustrate alternative embodiments which include both a trocar tip and at least one tapered portion. For example, FIG. 2 includes a "neck" within the distal portion 12 which provides for greater flexibility because the neck has a narrower diameter than the rest of the pin—for example, the neck may have a diameter of about 1.5-2.0 mm, while the trocar tip and shaft of the pin may have a diameter of about 2.1-2.5 mm and more specifically about 2.4 mm. FIG. 4 illustrates an embodiment having a single taper from the larger diameter of the trocar tip (for example, about 2.4 mm), to the smaller diameter of the shaft (for example, about 2.2 mm).

The flexible pin 10, 110, 210 may be flexible to allow for bending to form a curved path between, for example, a first and second bone, such as a tibia and a femur, or through and along a curved path of a cannulated instrument. The pin 10, 110, 210 should not be too stiff because it could have trouble obtaining the required bend to reach the desired anatomical location. Likewise, the pin should not be too flexible as it will have too little strength to penetrate bone and/or dense soft tissue. In one example, the pin 10, 110, 210 may be made of Nitinol which is flexible enough to maintain a bend along at least a portion of its length to the correct anatomical location. Likewise, Nitinol is strong enough to puncture bone and/or soft tissue. Moreover, Nitinol may have shape memory characteristics which allow the pin 10, 110, 210 to be "set," meaning that at a certain temperature, the pin 10, 110, 210 can become more or less stiff/flexible. For example, it may be desired that the pin be more flexible prior to an action such as drilling (using a power drill connection) to allow for easier placement of the pin to the anatomical location. Once drilling begins, it may be desirable for the pin to be more rigid to more easily penetrate the bone and/or soft tissue despite the bend in the pin between the two bones, as well as to drill the bone tunnel along a generally straight and substantially linear path (for example, a bend may be present between the bones, but within the bones the tunnels may be generally straight). Therefore, to obtain these desired results in this example, the Nitinol pin is used because Nitinol may have "shape memory" characteristics. To utilize the shape memory characteristics, the Nitinol flexible pin is designed to have a "set temperature" which may be slightly higher than body temperature (for example, between 40 and 60 degrees Celcius). Thus, at a lower temperature, below the set temperature, the flexible pin is flexible and can be easily bent from its original, generally straight and substantially linear shape. However, at a higher temperature, above the set temperature, the flexible pin becomes less flexible, and further if, upon heating, is in a bent position, will tend to return to its original, generally straight and substantially linear shape. Thus, prior to drilling the flexible pin into the femur, the flexible pin would be at the lower temperature, and can easily bend between the tibia and femur, or through a curved cannulated guide. But once drilling into the femur commences, the distal portion of the flexible pin, upon entering the femur, will increase in temperature to above the set temperature, which causes this distal portion of the pin to tend to return to its original generally straight and substantially linear shape, which results in a generally straight and substantially linear femoral tunnel path. If the flexible pin is drilled into the tibia to form a tibial tunnel path, heating would also occur thus causing the pin to form a generally straight and substantially linear path through the tibia.

Figure 5:
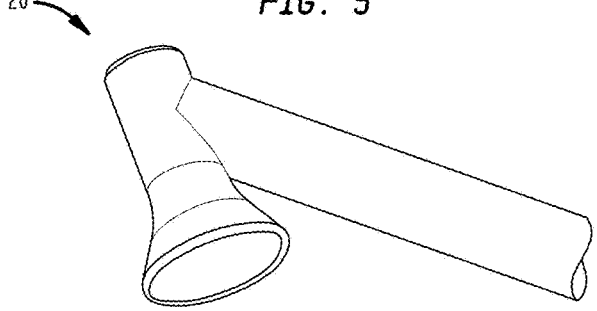
FIGS. 5, 6, 7 and 8 (FIG. 8 illustrated as a photograph) illustrate various embodiments of femoral aimers.
Figure 6:
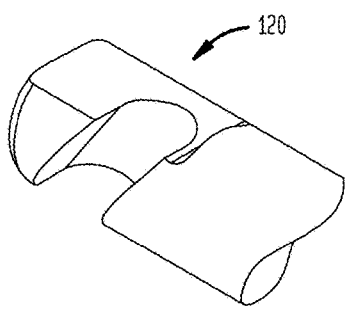
Figure 7:
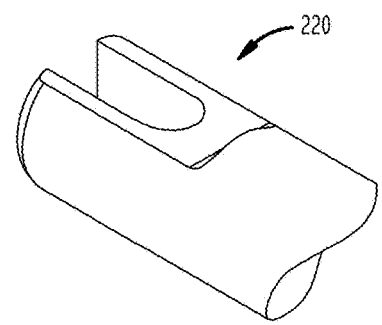
Figure 8:
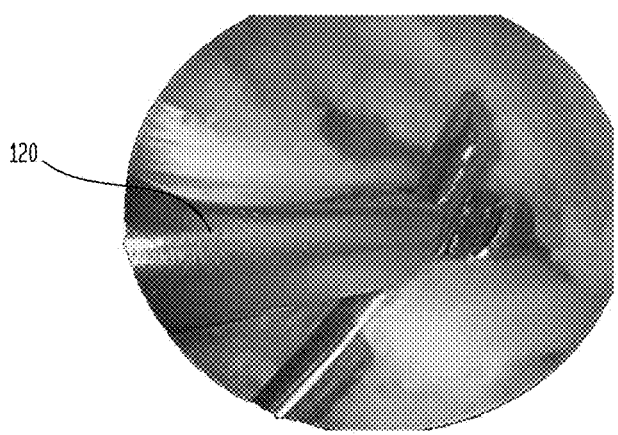

The instrumentation system may further include a femoral aimer which may engage the flexible pin and alter the trajectory of the pin within a joint. To continue the example of ACL repair, the femoral aimer may be used to bend the pin to have a curved path, which may be extending from the tibia or from a location outside of the joint, to the anatomical location for entry into the femur. Various embodiments of femoral aimers 20, 120, 220 are illustrated in FIGS. 5-8, in which each of the aimers may substantially surround, or alternatively, completely surround, a circumference of the flexible pin. FIG. 5 illustrates a funnel-shaped aimer 20 in which the pin is positioned within the funnel, and the funnel is then rotated to bend the pin along a curved path to the proper anatomical location on the femur. FIGS. 6 and 8 illustrate a side-slot aimer 120 which is able to be easily disengaged from the pin since it does not completely surround the pin when pin is placed within the side slot. In an embodiment where the instrumentation comes as a kit, the kit may include both left and right side-slotted aimers 120 for added diversity of use. A further embodiment of a femoral aimer 220, as illustrated in FIG. 7, may include a forked tip within which the pin may be positioned.

Figure 9:
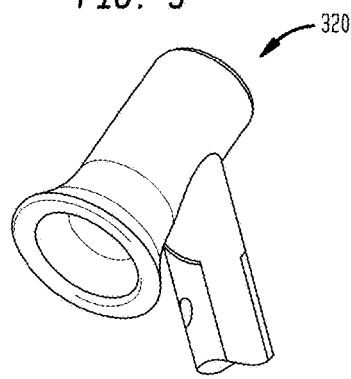
FIGS. 9, 10A, 10B, 10C, and 10D (illustrated as photographs) illustrate various embodiments of active femoral aimers.
Figure 10A:
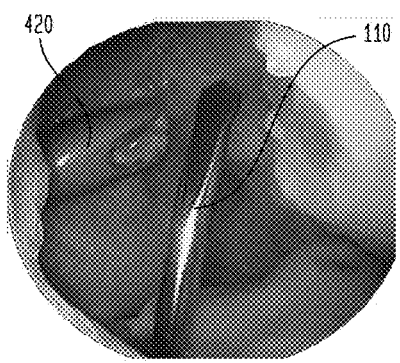
Figure 10B:
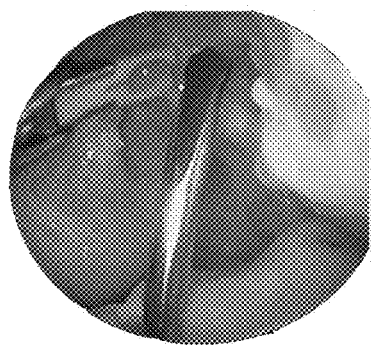
Figure 10C:
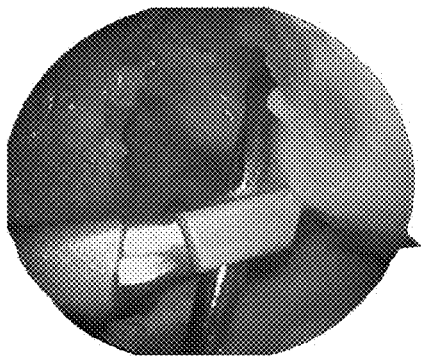
Figure 10D:
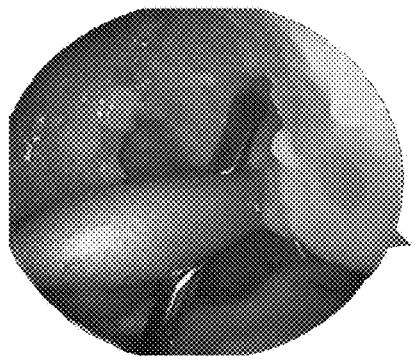
Figure 13:
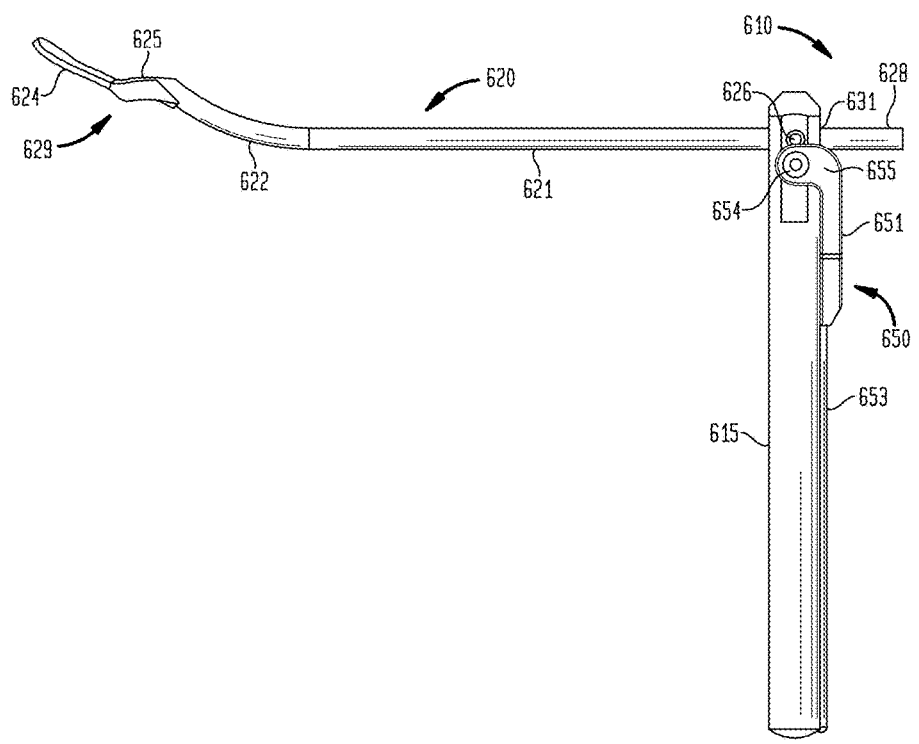
FIGS. 13, 14, 15, 16, 17 and 18 illustrate various views of a second embodiment of a curved guide tool of the present invention in various configurations.
Figure 14:
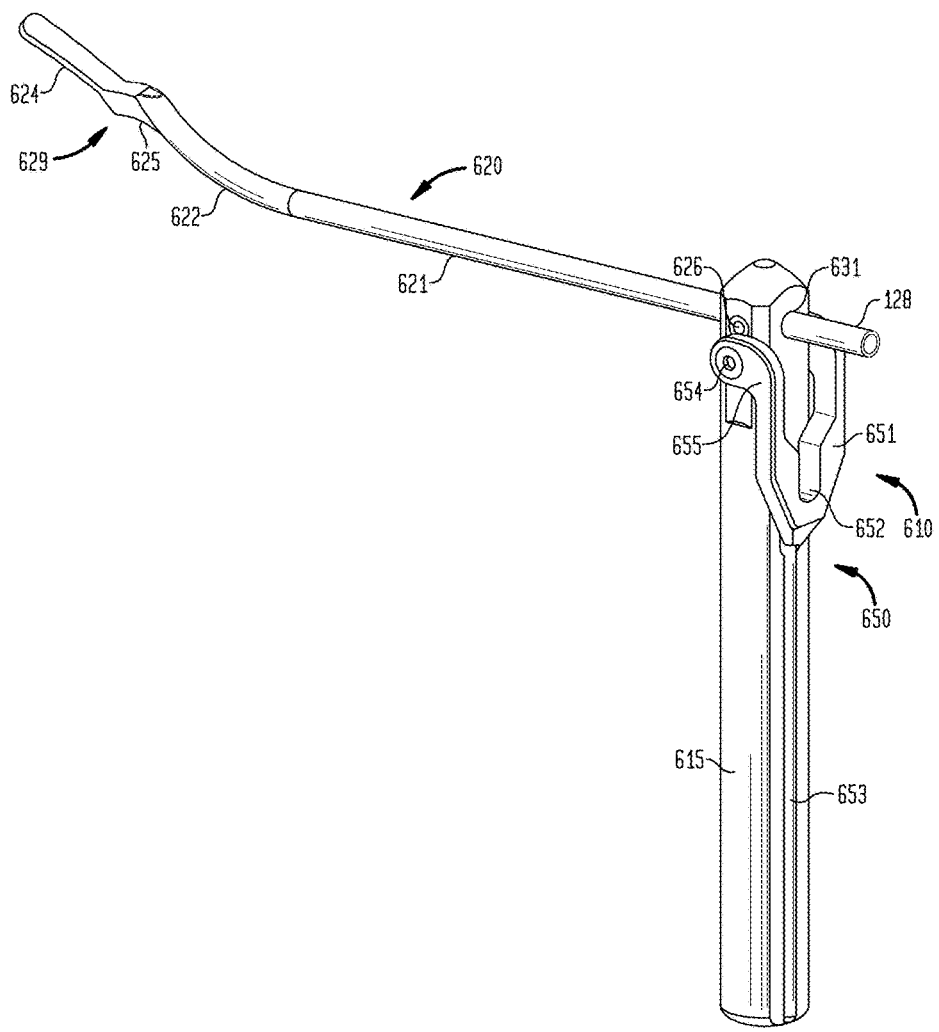
Figure 15:
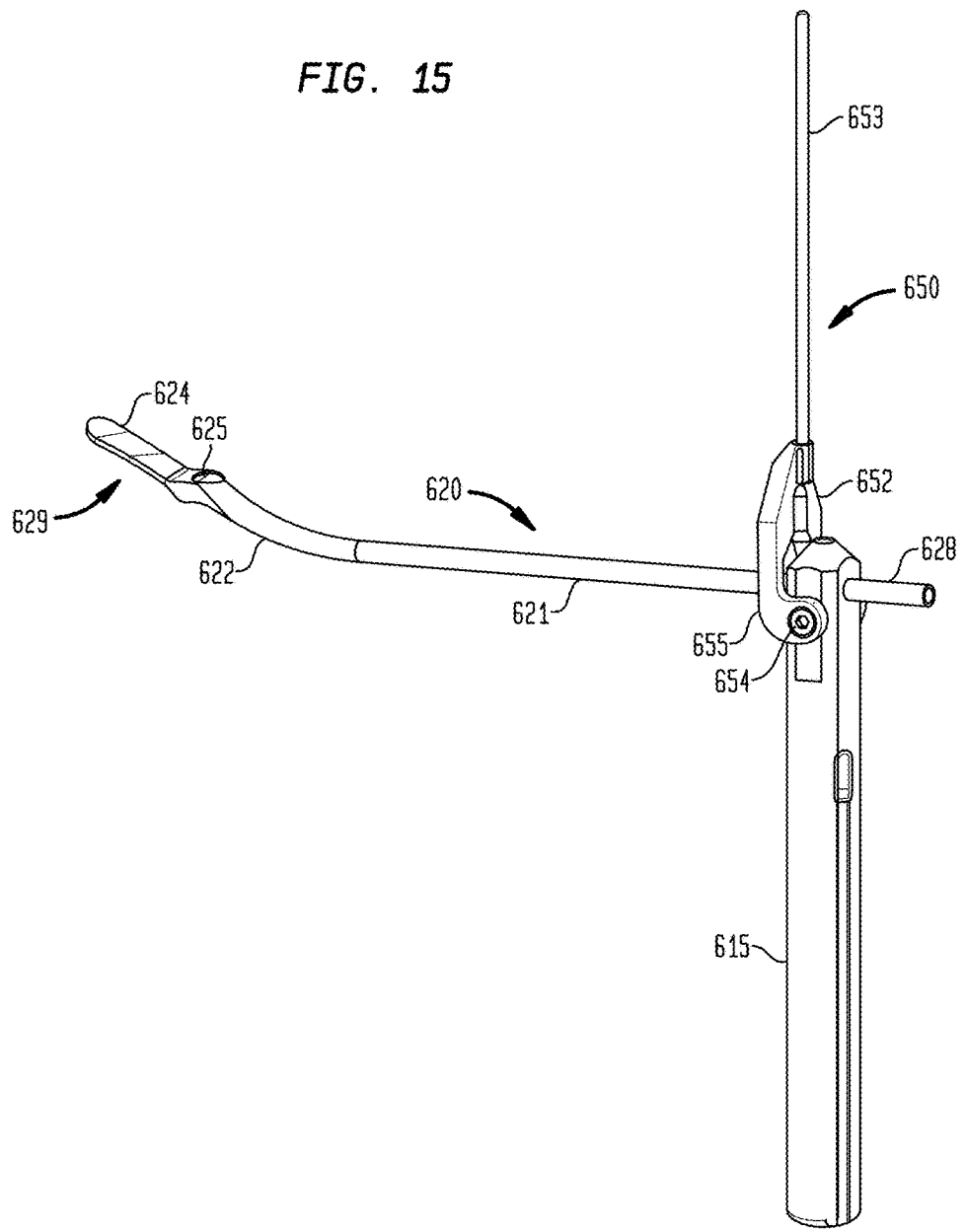
Figure 16:
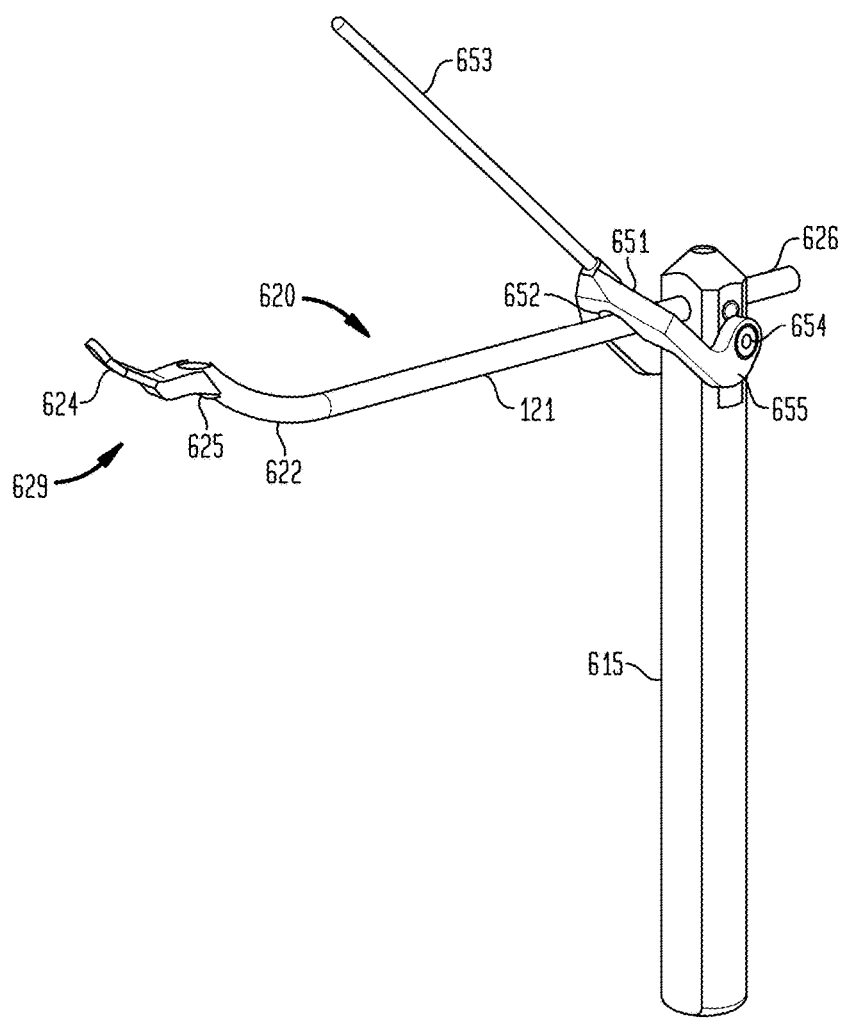
Figure 17:
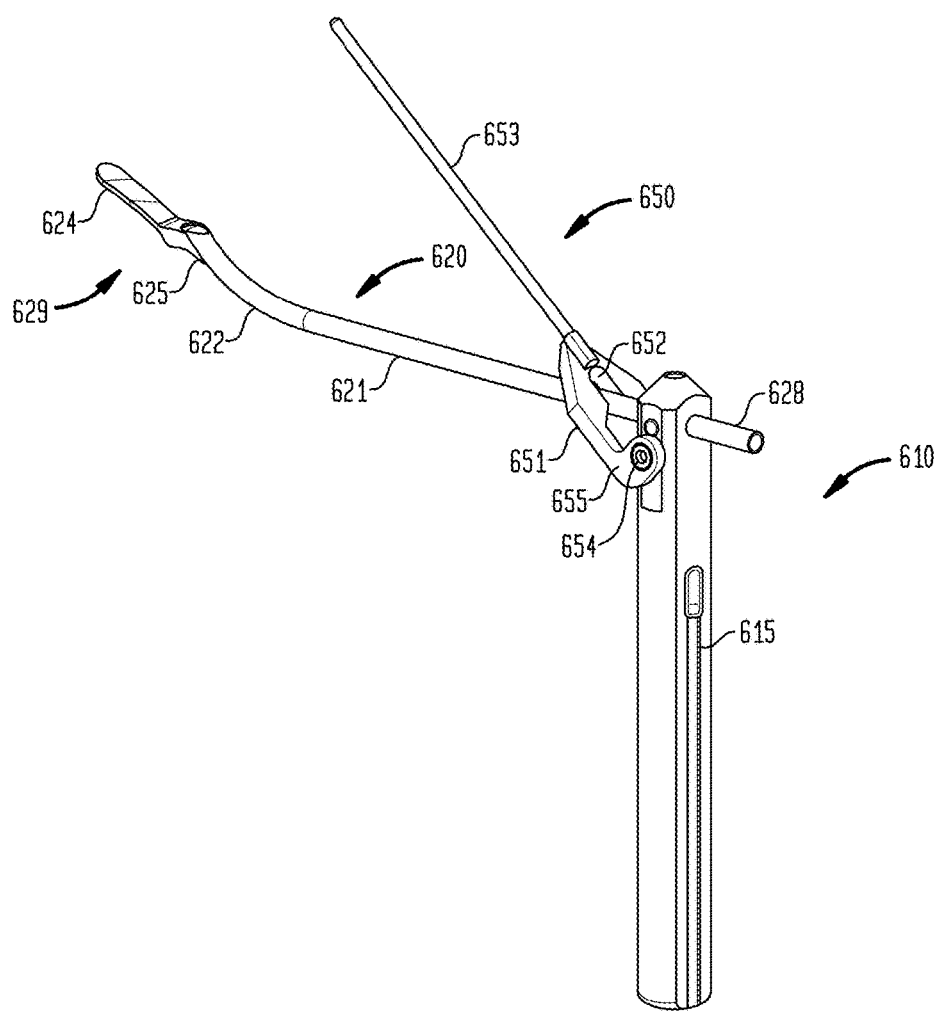
Figure 18:
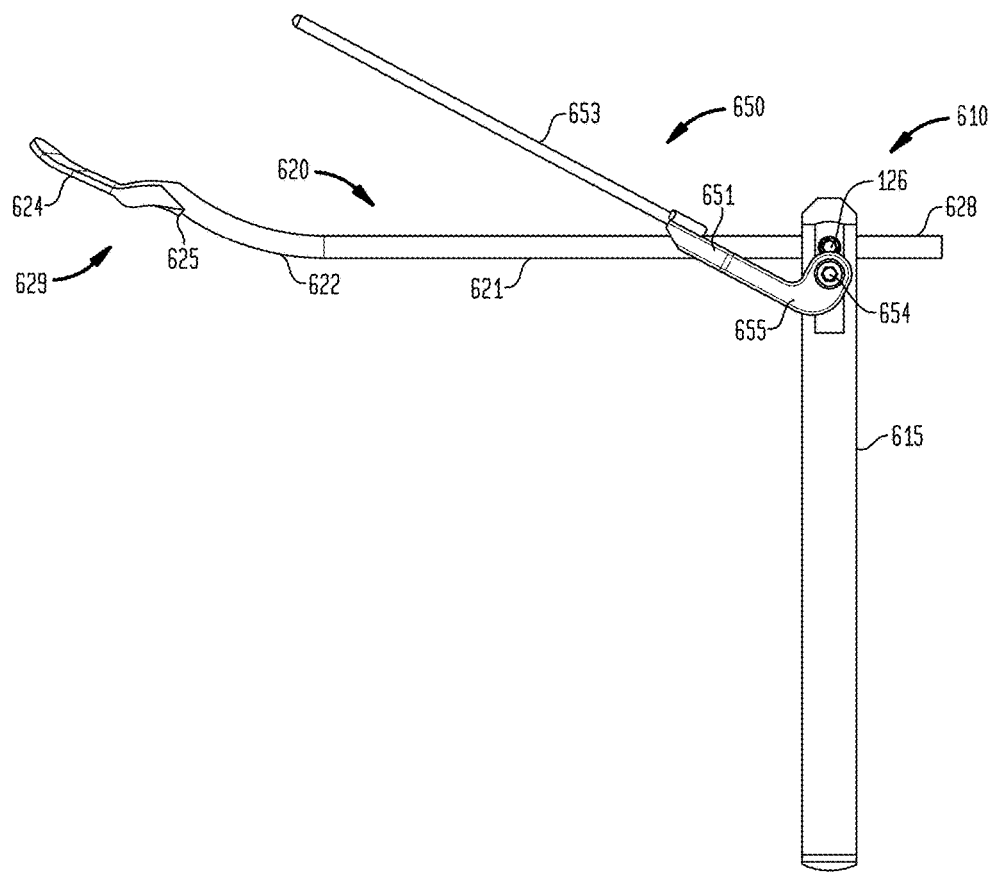
Figure 19A:
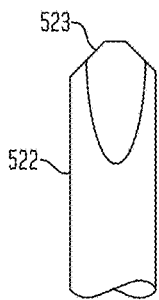
FIGS. 19A, 19B, 19C, 19D, 19E and 19F illustrate various configurations of a distal tip of one embodiment of a curved guide of the present invention.
Figure 19B:
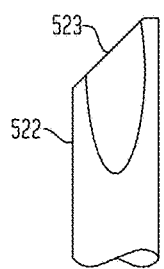
Figure 19C:
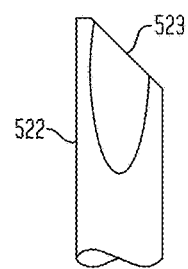
Figure 19D:
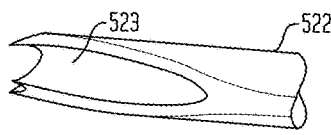
Figure 19E:
Figure 19F:
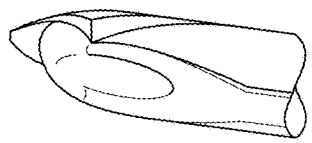

In yet another embodiment of a femoral aimer, FIGS. 9, 10A-D illustrate "active" aimers 320, 420. Active aimers 320, 420 may include a moveable tip portion that can attach and detach itself from the pin using any type of mechanical movement. Active aimers 320, 420 may, in some embodiments, be able to completely surround the pin during attachment, which may provide additional control of the pin during alteration of trajectory, while also being able to detach itself from the pin without regard to the actual position of the pin or the pin end portions. FIG. 9, for example, discloses a jaw type aimer which can open and close and which may completely surround the pin during use. FIGS. 10A-D disclose a further embodiment wherein the end portion of the aimer may have a disposable tip (for example, made of PEEK), which may be replaceable (so that the remainder of the aimer, which may be made of metal, may be reused). The disposable tip may be retractable/extendable from the end portion of the aimer.

Figure 20:
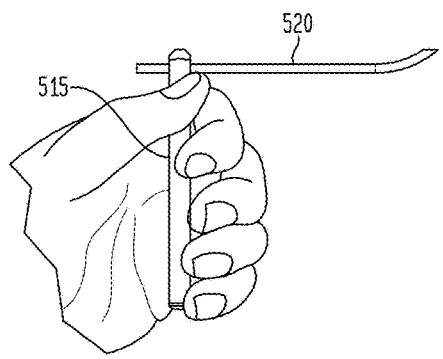
FIG. 20 illustrates one configuration of using an embodiment of a curved guide tool of the present invention.
Figure 21:
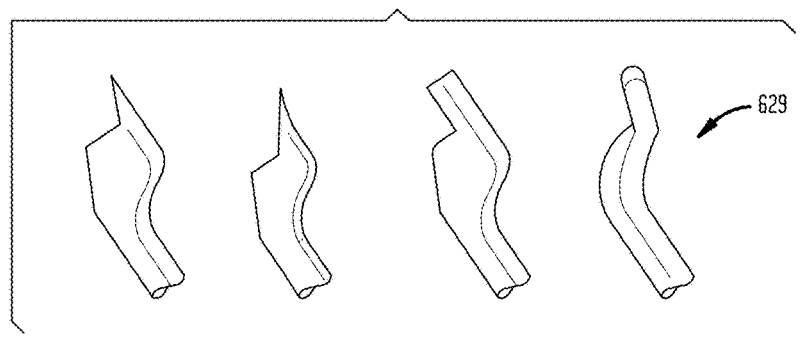
FIG. 21 illustrates various configurations of a flange on a distal portion of an embodiment of a curved guide of the present invention.
Figure 22A:
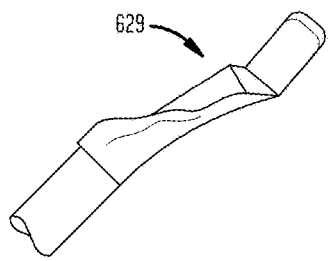
FIGS. 22A, 22B, 22C, 22D and 22E illustrate additional configurations of a flange on a distal portion of an embodiment of a curved guide of the present invention.
Figure 22B:
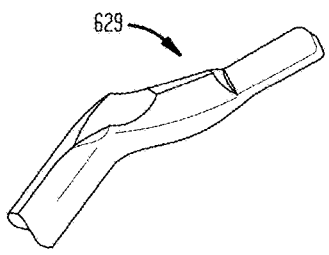
Figure 22C:
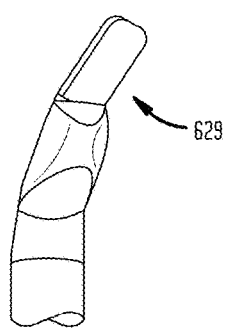
Figure 22D:
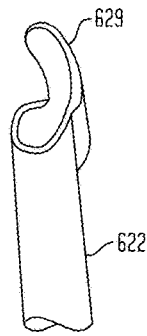
Figure 22E:
Figure 23:
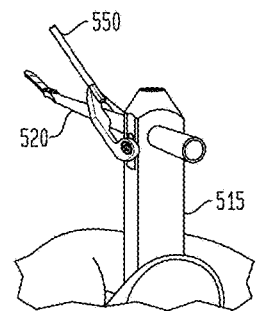
FIG. 23 is a proximal view of one embodiment of a curved guide tool of the present invention.

In another embodiment, an instrumentation system of the present invention may include a guide pin, such as the variations discussed above, and a curved guide tool 510, as illustrated in FIGS. 11 and 12. Curved guide tool 510 may include a handle 515, curved guide 520 and an outrigger 550. The curved guide tool 510 is operated by a surgeon grasping handle 515 (see FIG. 20). The curved guide 520 is positioned within a throughbore 531 in handle 515, such that a portion 528 of the guide 520 is proximal to the handle 515 and a portion 521 of the guide 520 is distal to the handle 515. A setscrew 526 secures guide 520 relative to handle 515. Alternatively, setscrew 526 may instead be a movable screw such that the screw may be loosened and the guide 520 can move in a distal-proximal direction relative to handle 515 or rotate on an axis of a linear portion (generally, 521, 528) of guide 520 relative to handle 515. The guide 520 includes a curved distal end 522 and may include a pointed distal tip 523. As further illustrated in FIG. 11, portion 521 of guide 520 is coincident with a first axis 580 while a guide path through curved distal end 522 of guide 520 proximal to distal tip 523 is coincident with a second axis 590. Distal tip 523 may be any arrangement of at least one point which is adapted to engage bone by, for example, digging into bone surface. FIGS. 19A-F illustrate various configurations of distal tip 523. The guide 520 is hollow, and preferably cannulated along its entire length, to provide for the passage of, for example, a flexible drill pin or guide wire, therethrough.

The outrigger 550 includes a swivel connection 554, which may connect outrigger main body 551 to handle 515. The main body 551 may include an opening 552. Outrigger 550 also includes an extension 553, having a longitudinal axis along its length. As seen from FIG. 11 to FIG. 12, with curved guide secured to handle 515 through setscrew 526, outrigger 550 may swivel at connection 554 at least from the body of the handle 515 around to the body of the curved guide 520, where guide 520 may nest within opening 552 at a maximum range of outrigger 550 motion towards guide 520. Outrigger 550, throughout its swivel range, remains along the general plane of the guide tool 510, wherein the plane is defined generally along the longitudinal axes of all of handle 515, guide 520, and outrigger 550. Opening 552 in main body 551 also allows outrigger 550 to pass over the portion 528 of curved guide 520. In the embodiment of curved guide 520 connected to handle 515 through a movable screw, curved guide 520 should be positioned sufficiently in the distal direction, relative to handle 515, to shorten the length of portion 528 to allow passage through opening 552. The movable screw may be loosened to adjust the distal-proximal arrangement of curved guide 520 relative to handle 515. Once outrigger 550 moves over portion 528, surgeon may then readjust the distal-proximal arrangement of curved guide 520 relative to handle 515 as needed.

FIGS. 13-18 illustrate a further embodiment of the curved guide tool of the present invention. In this embodiment, curved guide tool 610 includes a handle 615, curved guide 620 and an outrigger 650. The curved guide tool 610 is operated by a surgeon grasping handle 615. The curved guide 620 is positioned within a throughbore 631 in handle 615, such that a portion 628 of the guide 620 is proximal to the handle 615 and a portion 621 of the guide 620 is distal to the handle 615. A setscrew 626 secures guide 620 relative to handle 615. Alternatively, setscrew 626 may instead be a movable screw such that the screw may be loosened and guide 620 can move in the distal-proximal direction relative to handle 615 or rotate on an axis of a linear portion (generally, 621, 628) of guide 620 relative to handle 615.

The guide 620 includes a curved distal end 622 and may include a flange 629. Flange 629 is either integrally formed with the distal end 622 or is connected to the distal end 622 at connection site 625. The flange may have an offset from a longitudinal axis of the curved guide. The offset may further be at any angle, such as between about 0 and about 90 degrees, and more particularly at about 90 degrees. The flange may further include a second offset, positioned distal to the first offset. This offset, may be 0 degrees, more than 0 degrees, at least 20 degrees, at least 45 degrees, and most particularly about 45 degrees. The second offset may be in a different plane than the first offset, for example it may be in a plane that is orthogonal to that of the first offset. Additional examples of flanges within the scope of this invention are illustrated in FIGS. 21, 22A-E and 23. Flange 629 may also have a surface 624 which is generally adapted to index from soft or hard tissue within or near the joint, perhaps by engaging the tissue and perhaps even mating with a surface of the tissue. For example, the surface 624 may engage a portion of a lateral condyle on a femur in a knee joint (see FIG. 28). In one embodiment, the surface 624 may have a shape that matches in some manner with the shape of the tissue, for example, the shape of a condyle. Thus, as in the various FIGS. 13-18, 21-23, and 28), flange may have a complex geometric shape, to match the corresponding anatomy of the condyle. It is also envisioned that other shaped flanges may be used depending on the certain anatomy involved in a surgical procedure at a specific location in the patient.

The guide 620 is hollow, and preferably cannulated along its entire length, to provide for the passage of, for example, a flexible drill pin or guide wire, therethrough. The outrigger 650 may include a swivel connection 654, connecting outrigger main body 651 to handle 615. The main body 651 may include an opening 652. Outrigger 650 also includes an extension 653, having a longitudinal axis along its length. As seen from FIGS. 13, 15, and 16, with curved guide 620 secured to handle 615 through setscrew 626, for example, outrigger 650 may swivel at connection 654 at least from the body of the handle 615 around to the body of the curved guide 620, where guide 620 may nest within opening 652 at a maximum range of outrigger 650 motion towards guide 620. Outrigger 650, throughout its swivel range, remains along the general plane of the guide tool 610, wherein the plane is defined generally along the longitudinal axes of all of handle 615, guide 620, and outrigger 650. Opening 652 in main body 651 also allows outrigger 650 to pass over the portion 628 of curved guide 620. In the embodiment of curved guide 620 connected to handle 615 through a movable screw, curved guide 620 is positioned sufficiently in the distal direction, relative to handle 615, to shorten the length of portion 628 to allow passage through opening 652. The movable screw may be loosened to adjust the distal-proximal arrangement of curved guide 620 relative to handle 615. Once outrigger 650 moves over portion 628, surgeon may then readjust the distal-proximal arrangement of curved guide 620 relative to handle 615 as needed.

In yet a further embodiment, curved guide tool 810 may include, as illustrated in FIGS. 29-34, a handle 815, cannulated guide 820 and a plug 812. The cannulated guide tool 810 may further include an outrigger 850. The cannulated guide tool 810 is operated by a surgeon grasping handle 815. The guide 820 may be hollow, having a cannulated opening preferably along its entire length, and further through the handle 815, and to a cannula entry 825, to provide for the passage of, for example, a flexible drill pin or guide wire, therethrough.

Figure 31:
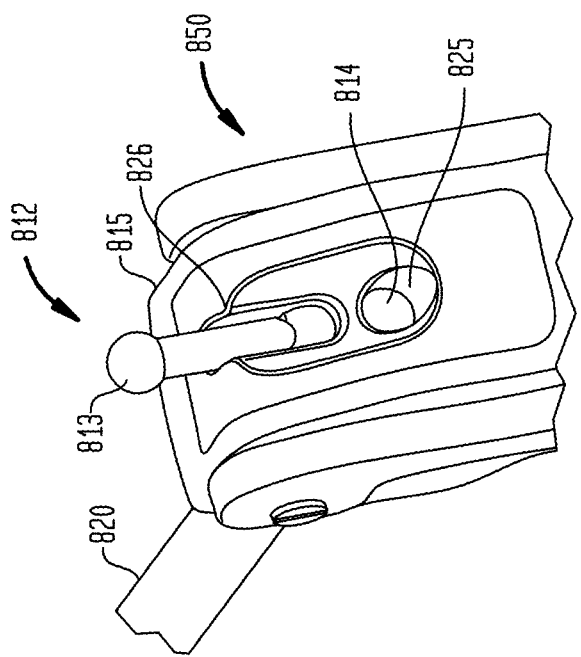

The plug 812 may be positioned within the cannulated opening of cannulated guide 820, the cannulated opening may pass completely through the entire length of the tool 810, from a distal end 828 of cannulated guide 820 to a cannula entry 825 at a proximal end of tool 810. As illustrated in FIG. 31, plug 812 may be positioned towards the proximal end of tool 810, and generally within handle 815, though other positions along the cannulated opening are envisioned.

Figure 32:
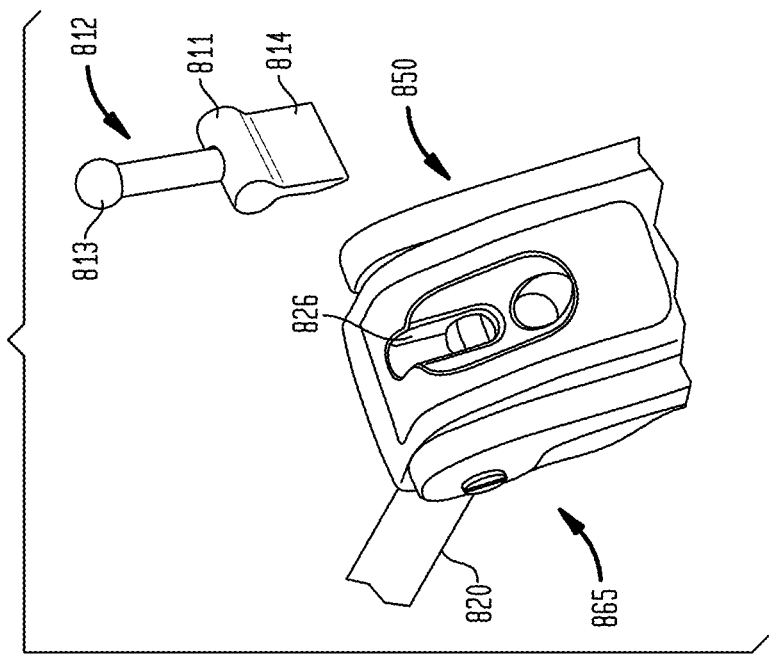
FIG. 32 illustrates an exploded view of the cannulated guide tool of FIG. 29 in which an embodiment of a plug is separated from the cannulated guide tool.
Figure 33:
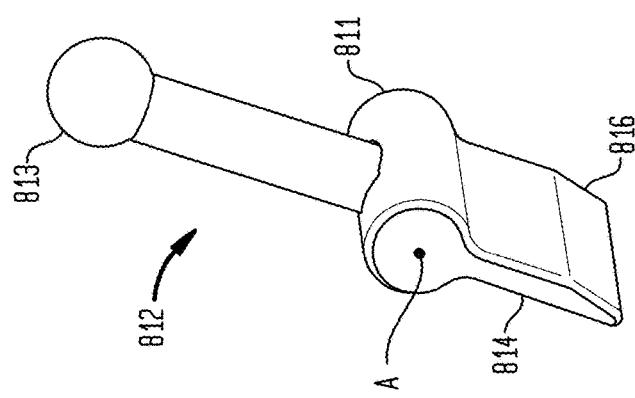
FIG. 33 illustrates one embodiment of a plug of the present invention.

As illustrated in FIGS. 32 and 33, plug 812 may include a dam 814 and a pivot 811. Plug 812 is positioned relative to the cannulated opening such that dam 814 may, at a closed position, be positioned to substantially block the path of the cannulated opening (see FIG. 31). Dam 814 may be pivoted away from the path of the cannulated opening by rotation at pivot 811, along axis A, to an open position where the cannulated opening path is substantially clear relative to dam 814. Plug 812 may include various arrangements for controlling the position of dam 814. As illustrated in FIGS. 31-33, plug 812 may include a manual activation 813, controllable by, for example, a thumb of the surgeon. As the plug 812 is pivoted, the manual activation 813 may travel through a manual activation groove 826 in the handle 815. Groove 826 is of a sufficient size to allow the manual activation 813 a full range of motion sufficient to pivot dam 814 from the closed position to the open position.

Figure 34A:
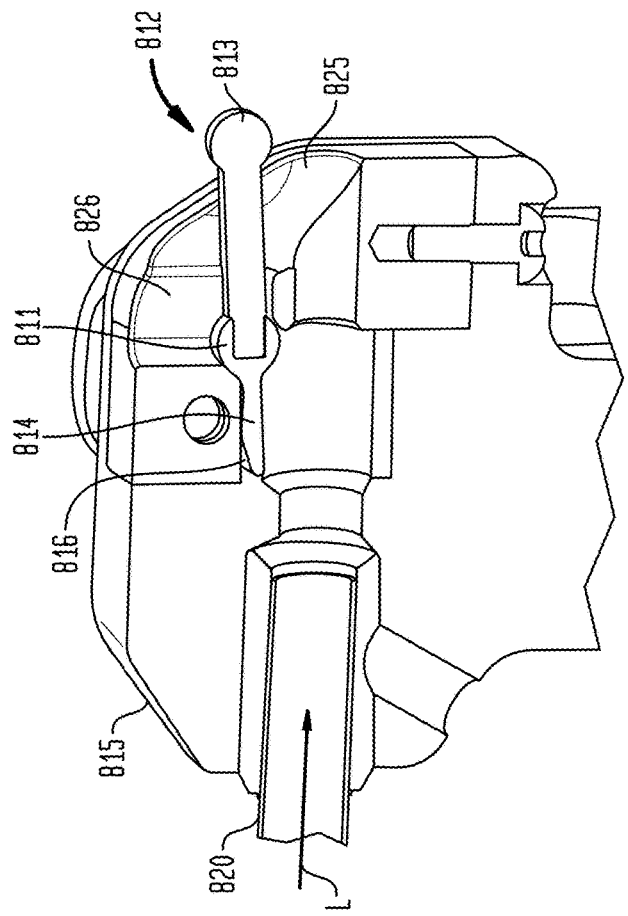
FIGS. 34A, 34B and 34C are cross-sectional views of one embodiment of a cannulated guide tool illustrating one use of the plug therein.
Figure 34B:
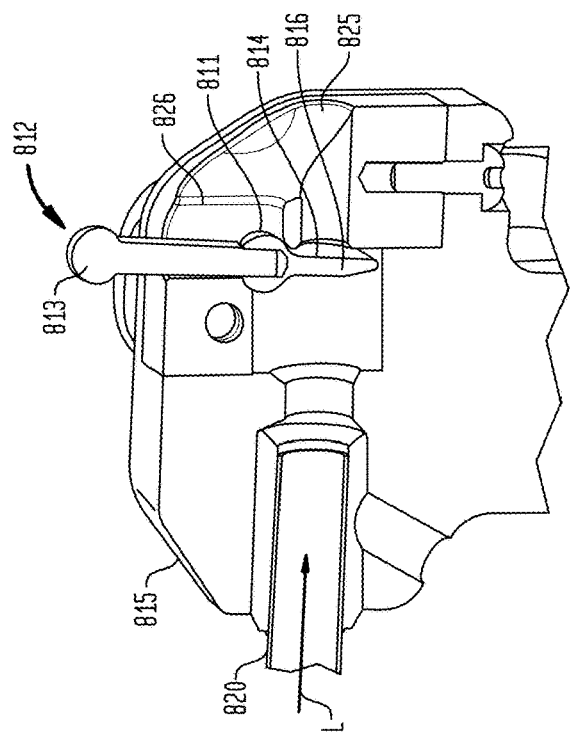
Figure 34C:
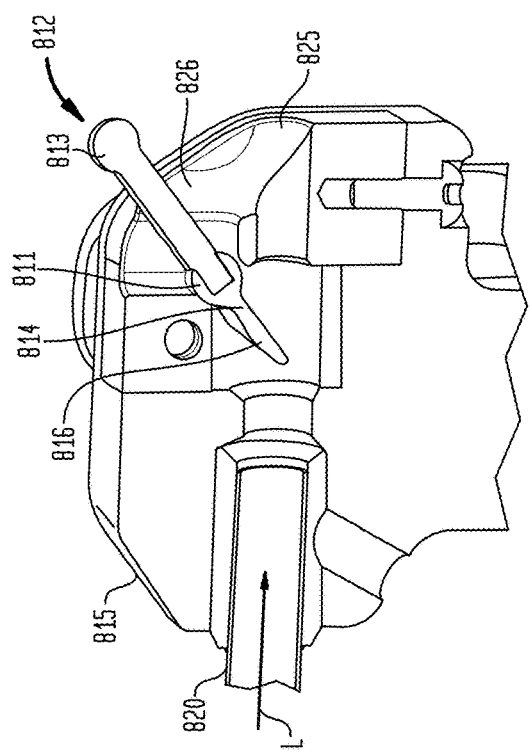
Figure 35A:
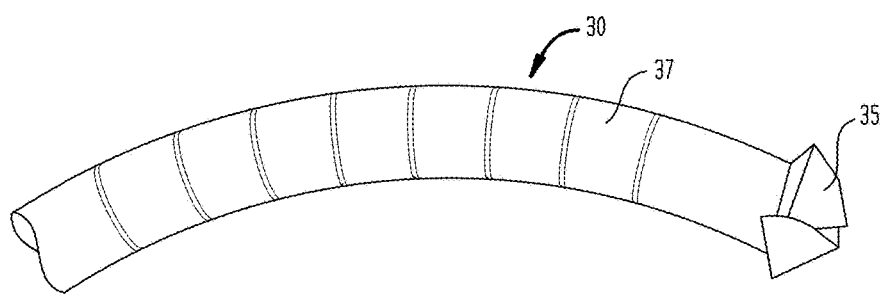
FIGS. 35A, 35B, 36A, 36B and 36C (FIGS. 35A and 35B illustrated as photographs) illustrate various embodiments of a flexible reamer of the present invention.
Figure 35B:
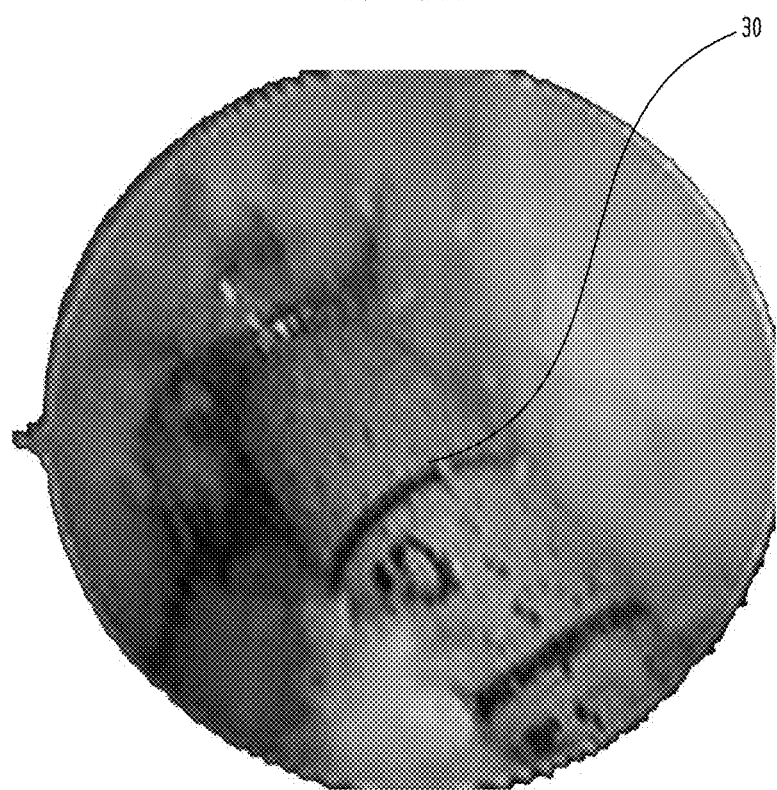
Figure 36A:
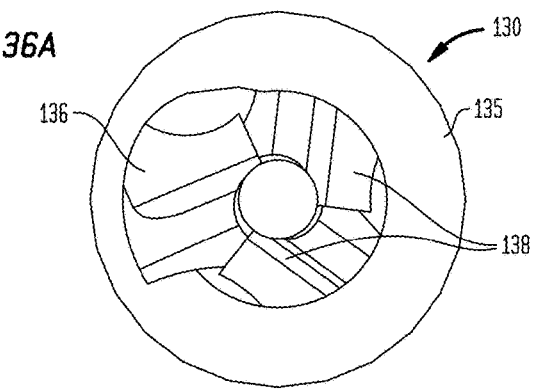
Figure 36B:
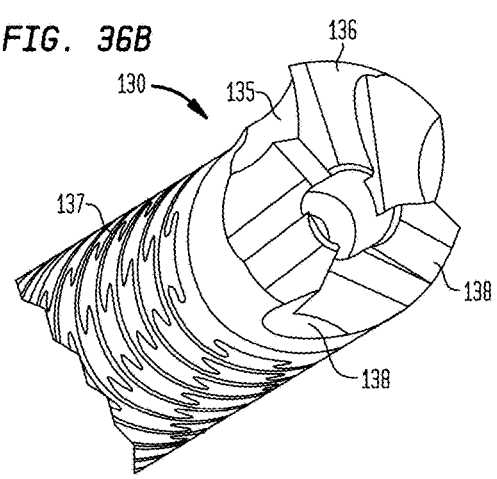
Figure 36C:
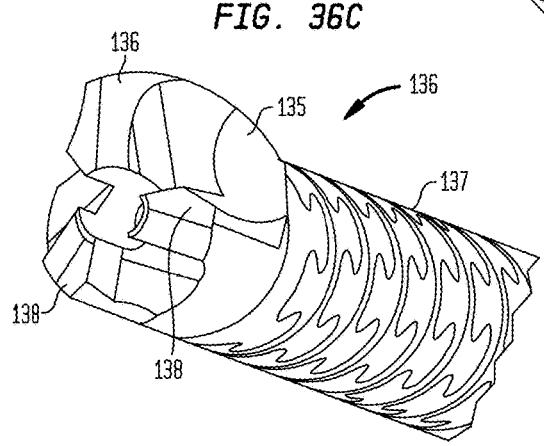

FIGS. 34A-C further illustrate this embodiment of plug 812. FIG. 34A illustrates the dam 814 at the open position, such that the path of the cannulated opening is substantially clear. FIG. 34B illustrates the rotation of dam 814 around pivot 811 as dam 814 rotates from the open position to the closed position. FIG. 34C illustrates dam 814 at the closed position, wherein the dam substantially blocks the path of the cannulated opening.

It is envisioned that other types of valves or dams may also be used for plug 812, such as a knife valve, which, rather than pivoting on an axis, moves along a plane, in an up and down motion, perpendicular to the path of the cannulated opening. The surgeon may be able to manually control the up and down motion of the dam. Alternatively, the valve could be a butterfly valve, wherein the dam would be split into two portions, and each portion is hinged along a central, stationary, support. Each dam portion can be manually actuated or be spring loaded. Other forms of valves, dams or the like are also envisioned.

In another embodiment to the plug 812 illustrated in the Figures, rather than the manual activation, the dam 814 may be spring loaded, or the like, such that it may be biased towards either the closed position or the open position.

Specifically, plug 812 is intended to maintain adequate clear liquid pressure inside the joint, during arthroscopic surgery, to maintain visibility for the surgeon by forcing blood and other debris from the joint. Clear liquids used by surgeons in arthroscopic surgery include saline, Ringers solution, and the like.

In use, plug 812 is intended to limit the amount of clear fluid, the flow of which is designated at "L" in FIGS. 34A-C, which exits the joint through the cannulated guide tool 810 through the cannulated opening and out the cannula entry 825 while still permitting the surgeon to utilize the tool 810 to, for example, pass a surgical instrument, or the like, through the cannula entry 825 and into the cannulated opening and into the joint. Thus, plug 812 is intended to be in the closed position when the surgeon has positioned the tool 810 in or adjacent the joint, but is not prepared to utilize the tool 810 or the cannulated opening. When the plug 812 is in the closed position (FIG. 34C), the dam 814 substantially prevents the flow of clear liquid from the cannula entry 825. Then, when the surgeon is prepared to use tool 810, for example, in passing a pin through the cannulated opening, the dam 814 may be opened to allow the passage of the surgical instrument. Of course, it is expected that some fluid loss may occur when using the tool 810 and when the dam 814 is in the open position.

The dam 814 may be opened or closed by the surgeon using the manual activation 813. Additionally, the dam 814 may pivot semi-automatically. For example, as in FIG. 34B, if dam 814 were positioned somewhere in between the open and closed position, the force of the clear liquid flow L passing up through the cannulated opening may contact a distal face of the dam 814, whereby the dam 814 is forced to the closed position, which in turn prevents further flow of liquid out of the joint and to cannula entry 825. Moreover, the distal face of dam 814 may include a taper 816, which may provide increased pressure on the distal face of the dam 814 by the clear liquid. Taper 816 may also be useful in assisting the dam 814 to pivot to the closed position when dam 814 is closer to the open position, and possibly even when the dam 814 is substantially in the open position. This may particularly be important in the event the surgeon is not using tool 810, but neglected to pivot dam 814 to the closed position manually. Of course, plug 812 may also include a spring bias (not shown) towards, for example, the closed position, to prevent such an oversight by the surgeon and ensure adequate clear liquid pressure is maintained inside the joint.

When the surgeon is ready to use the tool 810, the dam 814 may be opened manually, using manual activation 813 or by physically pressing the instrument against a proximal face of the dam 814, forcing dam 814 into the open position. Pressing the instrument against the proximal face of dam 814 may also be used when a spring bias is holding the dam 814 in the closed position, though of course, the manual activation 813 may still be present and used in conjunction with the spring bias.

Plug 812 also allows the surgeon to do multiple tasks at once, as the use of plug 812 frees up a hand of the surgeon, or assistant, who ordinarily may have to, for example, place a thumb at the cannula entry 825 to prevent loss of clear liquid from the joint when the surgeon is not using tool 810. Plug 812 also allows the surgeon to use one hand to control the tool 810 in that the surgeon may grip the handle and use a thumb to open or close plug 812 as desired.

Any of the above exemplary instrumentation systems may further include a flexible reamer 30, 130. As illustrated in FIGS. 35A-B and 36A-C, flexible reamer 30, 130 includes a shaft 37, 137 which may include a flexible portion. The flexible portion is made by taking metal tubing and forming a laser cut in the metal to a sufficient depth to allow flexing about the cut. The laser cut may extend circumferentially around the outer surface of the tubing and may have a wave or sinusoidal shape to enhance flexibility. The flexible portion is then laser welded to a tip 35, 135. In a further embodiment, the laser cuts may pass completely through the tubing to form discrete, interlocking portions of tubing which may be interlocked by the shape of the cuts, for example, like jig-saw puzzle pieces, such that shaft 37, 137 may be a single piece, and the laser cut may then be applied to the tubing to form the flexible portion. Each jig-saw puzzle piece may be a fraction offset from the pieces above and below to improve stability and may also provide a smooth function of the reamer. At the distal end of the flexible shaft 37, 137 is the tip 35, 135 which may be laser welded. The tip 35, 135 may have a diameter for producing a pilot hole on the surface of the bone, and may further create the tibial and/or femoral tunnel (as discussed below, in some methods, the tibial tunnel may be formed using a typical stiff-shafted reamer). The entire reamer 30, 130 may be cannulated such that reamer may be positioned over the pin, such that the pin is within the cannulated portion, which may allow the reamer to travel along the pin and form the tibial and/or femoral tunnels. The cannulation along the flexible portion of the flexible reamer is such that the reamer may travel along the bent portion of the flexible pin such that the reamer may follow the curved path of the flexible pin. A proximal end of flexible reamer 30, 130 includes a drive element (not shown) which may be inserted into a standard power drill chuck. The proximal end of reamer 30, 130 may also include a stop feature to limit the depth of a pilot hole drilled in bone. The shaft of the reamer of this invention is also disclosed in co-pending patent applications, U.S. application Ser. No. 12/460,310, filed Jul. 16, 2009, by the same assignee as this patent application, entitled "Suture Anchor Implantation Instrumentation System," and U.S. application Ser. No. 12/821,504, filed Jun. 23, 2010, by the same assignee as this patent application, which is a continuation-in-part of U.S. application Ser. No. 12/460,310, the disclosures of which are hereby incorporated by reference herein as if fully set forth herein.

The tip 35, 135 of reamer 30, 130 may include at least one flute 136, such that the tip is asymmetric, for example, such that the flute 136 is off-axis relative to the longitudinal axis of the reamer (positioned towards one side of the tip). The single flute 136 may provide for easier entry and exit from a tunnel when going over a curved pin, and may further, for example, be positioned on the femur away from cartilage or other soft tissue located on the condyles or surrounding femoral surface. Furthermore, the tip may include additional smaller flutes 138. In one example, two additional flutes 138 are positioned on the tip. The tip remains asymmetrical, but the two additional flutes have numerous benefits including better continuity of the surface of the bone tunnel (less chance that a "thread pattern" results from asymmetrical drilling using a single flute), less wear on flute 136 and reduced breakage of the tip. In some embodiments, the diameter of the reamer is sufficiently larger than the outer diameter of the pin such that the reamer may have sufficient strength of material surrounding the cannulation (through which the pin is positioned).

The instrumentation system may include further instruments which may be used in soft tissue repair, such as, for example, straight stiff-shafted reamers, various types of suture, suture graspers, pin graspers, and the like.

The present invention also includes various surgical methods using the above-discussed instrumentation system for repair of soft tissue. As above, the exemplary surgical site will be for the preparation of bone tunnels for the repair and/or replacement of a damaged ACL. For all embodiments, a flexible pin constructed of Nitinol, or the like, may be used as such material may bend prior to passing into the femur and may still form a generally straight and substantially linear tunnel path through the femur.

In a first embodiment, the method of ACL repair may include forming a tibial tunnel through the tibia. The tibial tunnel may have any depth suitable to the surgery, soft tissue graft size, or the like. In one example, the diameter of the tunnel may be about 8-10 mm, though other sizes may be suitable as well. The tunnel may be directed in a proximal direction through the tibial plateau and may open into the knee joint. The tunnel may be formed using a drill (stiff or flexible shaft), reamer or the flexible reamer. The drill may then be removed from the tibia and a flexible pin may be passed up through the tibia. The pin should be passed through the tibia until a distal portion extends into the knee joint. An anterior-medial portal may also be formed through the skin to allow access into the knee joint. Typically, the anterior-medial portal will pass directly through the skin and into the joint, without passing through bone. A femoral aimer may be passed through the portal and positioned within the knee joint. As the distal portion of the pin enters the joint (such that, for example, about 10-20 mm of the distal portion of the pin is exposed within the joint), the femoral aimer may interact with the pin to engage the distal portion of the pin and adjust the trajectory of the pin to bend and guide it towards a desired location on the femur.

Optionally, the desired location on the femur may be marked using a starter awl, or other instrument, to form a pilot divot. Various methods of using the starter awl may be used. One example would be to use the femoral aimer to determine the proper location for the femoral tunnel to ensure the tunnel will have a sufficient "back wall" (i.e., the posterior side of the femur) Then, a standard drill (i.e., 2.4 mm) penetrates the femur at the desired location to a depth of a few millimeters. The drill is then removed and the awl is used to widen the tap to about 4 mm. A second exemplary use of the awl would be to use the awl freehand and judge, using visual cues and experience, the back wall distance and proper location of the femoral tunnel. A third exemplary use of the awl would be to use a microfracture pick, or the like, freehand and judge, using visual cues and experience, the back wall distance and proper location of the femoral tunnel. Then, the microfracture pick should be removed and the awl is used to widen the tap to about 4 mm.

Once the pin is placed against the femur (whether or not the awl was used to create a pilot divot), the pin may be passed through the femur until it exits the femur, proximal to the knee joint, and through the adjacent skin. For example, the pin may be attached to an electric drill and drilled into the femur to a depth of about 20 mm, at which time the aimer may be released from the pin, if possible. The pin is then drilled completely through the femur and out through the skin.

A flexible reamer (which may, for example, be cannulated) may then be positioned onto the pin such that the flexible reamer passes through the tibial tunnel and contacts the femur. The reamer may then be used to form a femoral tunnel to a specified depth, for example, about 30 mm, though as with all dimensions disclosed as to these methods, the depth may be dependent on the specific surgery and may thus be greater or less than 30 mm or may be sufficient for penetrating through the entire femur along the path of the pin. Leaving the pin in place, the reamer may then be removed from the femur and tibia. The pin may have a suture connector on its proximal portion (i.e., an eyelet or the like), through which a suture may be passed which may contain a soft tissue graft thereon. The pin is then pulled proximally, from where it exited the femur, to pull the suture and graft up through the tibial tunnel and into the femoral tunnel. The graft may then be secured.

In another embodiment, the method may include forming a tibial tunnel through the tibia, in any way known in the art. In one example, the diameter of the tunnel may be about 8-10 mm, though other sizes may be suitable as well. The tunnel may be directed in a proximal direction through the tibial plateau and may open into the knee joint. The tunnel may be formed using a drill. In alternate embodiments, the femoral tunnel (discussed below) may be reamed first, followed by the tibial tunnel.

The drill may then be removed from the tibia and a flexible pin may be passed up through the tibia. The pin should be passed through the tibia until a distal portion extends into the knee joint. An anterior-medial portal may also be formed through the skin to allow access into the knee joint. A femoral aimer may be passed through the portal and positioned within the knee joint. As the distal portion of the pin enters the joint, the femoral aimer may interact with the pin to adjust the trajectory of the pin and guide it towards a desired location on the femur. Optionally, the desired location on the femur may be marked using a starter awl, or other instrument, to form a pilot divot. Once the pin is placed against the femur, the pin may be passed through the femur until it exits out the femur, proximal to the knee joint, and through the adjacent skin. As above, the pin may be drilled into the femur, and the aimer, if possible, releases the pin once it is about 20 mm into the femur. The pin may have a suture connector on its proximal portion (i.e., an eyelet or the like), through which a suture is passed. The pin is then pulled proximally, from where it exited the femur, to pull the suture up through the tibial tunnel and into the joint space.

The suture and/or proximal portion of the pin may then be grasped by an instrument through the anterior-medial portal, and the pin may then be pulled backwards through the portal. A flexible reamer (which may, for example, be cannulated) may then be positioned onto the pin such that the flexible reamer passes through the portal and contacts the femur. The reamer may then be used to form a femoral tunnel to a specified depth (as above, about 30 mm, depending on the specifics of the surgical site). Leaving the pin in place, the reamer may then be removed from the femur and the portal. The pin may then be loaded with a free suture (through the suture connector) and pulled, from its distal end, back up through the femoral tunnel, until the proximal end, and attached suture, of the pin is visible within the knee joint. The attached suture may be grasped by an instrument, through the tibial tunnel, and the pin may then be moved distally back through the tibial tunnel, such that the suture and suture connector are outside the tibia on the distal end of the tibial tunnel. A suture, containing a graft, may be placed on the suture connector. The pin is then pulled proximally, from where the pin exited the femur, to pull the suture and graft up through the tibial tunnel and into the femoral tunnel. The soft tissue graft may then be secured by any means known in the art.

Alternatively, when reaming the femur through the anterior-medial portal, rather than first passing the flexible pin through the tibia, the pin may be immediately passed through the portal and positioned onto the femur, and stabilized, using the femoral aimer. The pin may then be drilled into the femur, as discussed above, followed by the use of the reamer to form the femoral tunnel, as above. The tibial tunnel may subsequently be prepared, and the graft may then be brought into place as above.

In yet another embodiment, the method may include passing a flexible pin through the tibia. The pin may be directed in a proximal direction through the tibial plateau and into the knee joint. Alternatively, the initial insertion of the pin may be done by drilling a rigid pin through the tibia and into the joint which may then be removed and replaced with a flexible pin. However, using the flexible pin even for the initial preparation of the tibial tunnel offers possible advantages in reducing the time required to drill the two tunnels. An anterior-medial portal may also be formed through the skin to allow access into the knee joint. A femoral aimer may be passed through the portal and positioned within the knee joint. As the distal portion of the pin enters the joint (about 15 to about 20 mm), the femoral aimer may interact with the pin to adjust the trajectory of the pin and guide it towards a desired location on the femur. Optionally, the desired location on the femur may be marked using a starter awl, or other instrument, to form a pilot divot. Once the pin is placed against the femur, the pin may be passed through the femur until it exits the femur, proximal to the knee joint, and through the adjacent skin. As in the above embodiments, the pin may be drilled into the femur, and once about 20 mm of the pin is within the femur, the aimer may release the pin, if possible.

A flexible reamer (which may, for example, be cannulated) may then be positioned onto the pin such that the flexible reamer follows the path of the pin and drills through the tibia and the femur in a single continuous motion to form a tibial tunnel and a femoral tunnel. The reamer diameter may be, for example, about 8-10 mm. The reamer may form a femoral tunnel to a specified depth. Leaving the pin in place, the reamer may then be removed from the femur and tibia. The pin may have a suture connector on its proximal portion (i.e., an eyelet or the like), through which a suture is passed which may contain a graft thereon. The pin is then pulled proximally, from where it exited the femur, to pull the suture and graft up through the tibial tunnel and into the femoral tunnel. The graft may then be secured.

In another embodiment, the method may include forming a tibial tunnel through the tibia. The tunnel may be directed in a proximal direction through the tibial plateau and may open into the knee joint. The tunnel may be formed using a drill with a diameter (i.e., about 5 mm) which is narrower than the diameter of the final tibial tunnel (i.e., about 8-10 mm), discussed below. The narrow-diameter drill may then be removed from the tibia and a flexible pin may be passed up through the tibia. The pin should be passed through the tibia until a distal portion extends into the knee joint. An anterior-medial portal may also be formed through the skin to allow access into the knee joint. A femoral aimer may be passed through the portal and positioned within the knee joint. As the distal portion of the pin enters the joint, to a depth of for example, about 10-20 mm, the femoral aimer may interact with the pin to adjust the trajectory of the pin and guide it towards a desired location on the femur. Of course, movement of the pin in the proximal/distal direction may be required, in coordination with the movement of the aimer, to properly align the pin with the femur. Optionally, the desired location on the femur may be marked using a starter awl, or other instrument, to form a pilot divot. Once the pin is placed against the femur, the pin may be passed through the femur until it exits the femur, proximal to the knee joint, and through the adjacent skin. As discussed in other embodiments of the method, the pin may be drilled to a depth of about 20 mm into the femur, at which point the aimer may release the pin. The pin is then drilled completely through the femur and skin.

A flexible reamer (which may, for example, be cannulated), having the larger diameter than the narrow-diameter drill, may then be positioned onto the pin such that the flexible reamer expands the diameter of the tibial tunnel and contacts the femur. This embodiment may allow the flexible pin to be more easily maneuvered through the initial small tibial drill hole compared to when the flexible pin was drilled directly through the tibia in an above embodiment. Moreover, the flexible reamer may have an easier time transitioning from the tibial tunnel to the femoral tunnel when compared to an embodiment where the tibial tunnel is drilled to its final diameter in a single pass. The reamer may then be used to form a femoral tunnel to a specified depth (i.e., about 30 mm). Leaving the pin in place, the reamer may then be removed from the femur and tibia. The pin may have a suture connector on its proximal portion (i.e., an eyelet or the like), through which a suture is passed which may contain a graft thereon. The pin is then pulled proximally, from where it exited the femur, to pull the suture and graft up through the tibial tunnel and into the femoral tunnel. The graft may then be secured.

In another embodiment, the instrumentation system may be used in a method of "all-inside" ACL repair. In this method, both the tibial and femoral tunnels are prepared from portals. For example, the femoral tunnel may be prepared using the method above where the tunnel is reamed directly through the anterior-medial portal. The tibial tunnel is likewise prepared through such a portal. First, a flexible pin is inserted through a superior portal and an aimer is inserted through an anterior portal (either medial or lateral). The pin may be directed to the tibial insertion site, and the aimer may bend the pin at the insertion site such that the pin is positioned towards the anterior surface of the tibia. The pin is then passed through the tibia (using a drill or the like), exiting out the anterior of the tibia. A flexible reamer (having a diameter of for example 8-10 mm) is then positioned on the pin and passes through the tibia to an appropriate depth from the interior of the joint (i.e., starting at the tibial plateau) and extending distally into the tibia. The pin, which may include a suture connector, is then used to guide a graft into the femoral and tibial tunnels, through the portal, and the graft is secured.

Figure 37A:
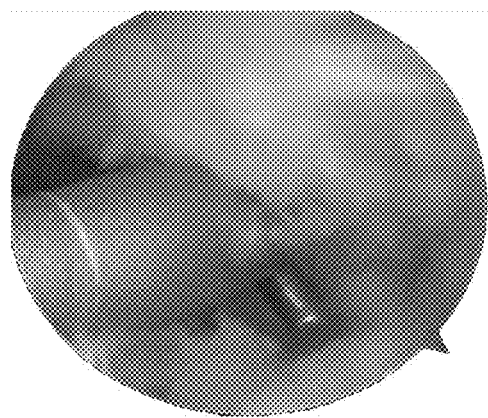
FIGS. 37A, 37B and 37C, illustrated as photographs, illustrate one embodiment of a method of tibial drilling in PCL repair surgery.
Figure 37B:
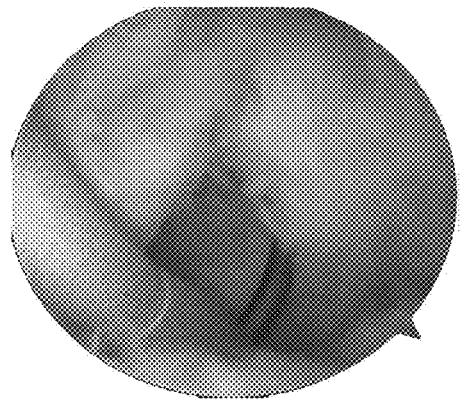
Figure 37C:
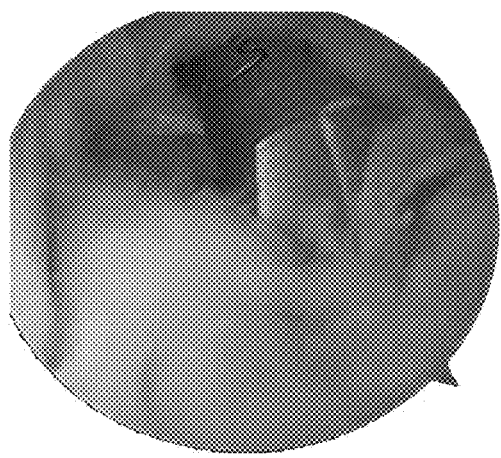
Figure 38A:
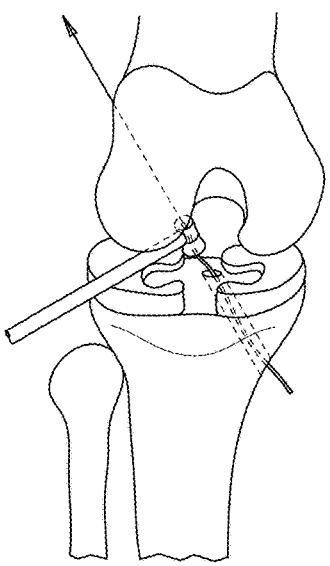
FIGS. 38A, 38B, 38C, 38D and 38E illustrate one embodiment of a method of ACL repair surgery.
Figure 38B:
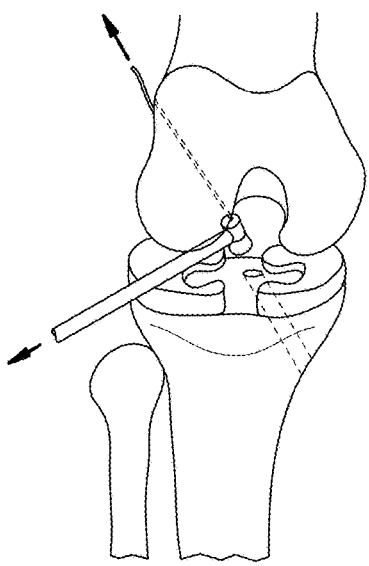
Figure 38C:
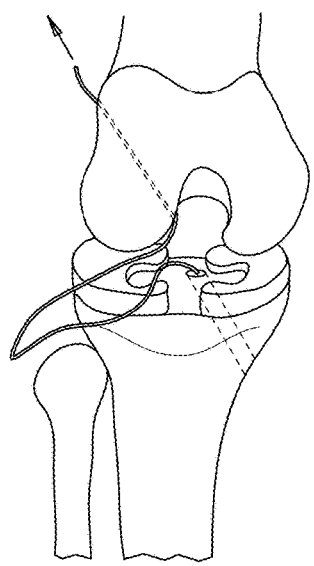
Figure 38D:
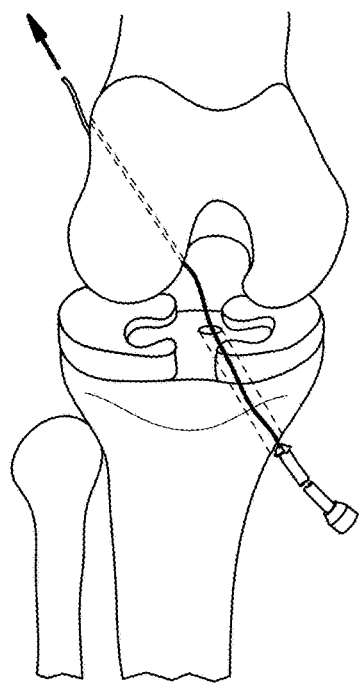
Figure 38E:
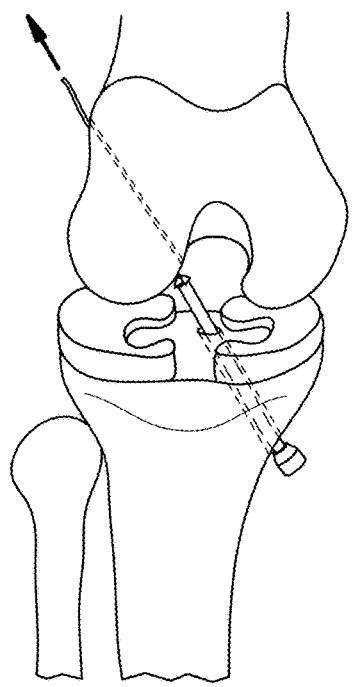

The present invention may also be used in soft tissue repair of other soft tissues in the body. For example, as illustrated in FIGS. 37A-C, the instrumentation system may be used to repair the Posterior Cruciate Ligament (PCL). In this method, a posterior (medial or lateral) portal may be created through the skin and into the knee joint, through which a flexible pin may be passed. An aimer may be directed through an anterior (medial or lateral) portal and into the knee joint as well. The aimer interacts with the pin and adjusts the trajectory of the pin from its position exiting the femur to contacting the posterior portion of the tibia, and towards the direction of the anterior portion of the tibia. The pin may then be passed through the tibia, by use of a drill for example, from the entry position on the posterior of the tibia to an exit location on the anterior portion of the tibia. A flexible reamer may then be placed over the pin to form the tunnels having a diameter of, for example, about 8-10 mm, until it passes completely through the tibia. Finally, using techniques known in the art, a graft may be placed within the tunnels and secured.

FIGS. 38A-E illustrate yet another embodiment of a method of using the instrumentation system. The main difference as compared to the above methods is illustrated in FIGS. 38B-E in which the flexible reamer passes along a heavy suture through the tibial tunnel and engages the flexible pin once within the joint.

Alternative methods of preparation of the femoral tunnel may also include the curved guide tool 510, 610, 810. The curved guide tool may be used, for example, in place of the femoral aimer to bend the flexible drill pin towards the proper location on the femur.

The curved guide tool 510, 610 may be used, in one embodiment, in a method of ACL repair. Specifically, the tool 510, 610 may be used to prepare the femur for reattachment of the torn ACL, attachment of a replacement graft ACL, or any similar procedure. In an exemplary embodiment, the preparation of the femur may include creating a generally straight and substantially linear tunnel in the femur at the desired site on the femur for subsequent attachment of the ACL graft within the tunnel.

Figure 24:
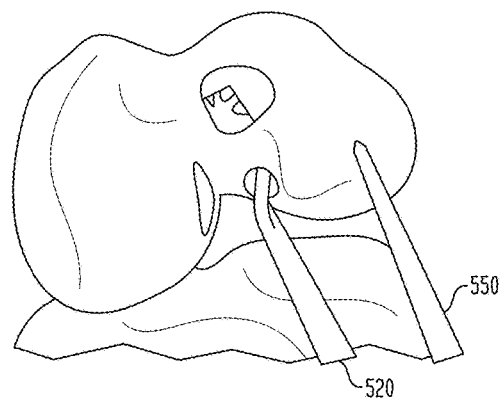
FIG. 24 illustrates one embodiment of a method of using an embodiment of a curved guide tool of the present invention on a knee joint.
Figure 25:
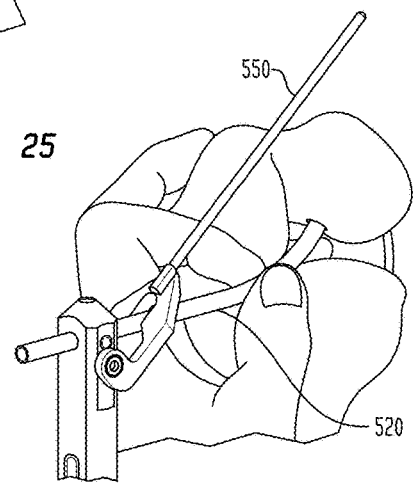
FIG. 25 illustrates an embodiment of a method of using an embodiment of a curved guide tool of the present invention on a knee joint.
Figure 26:
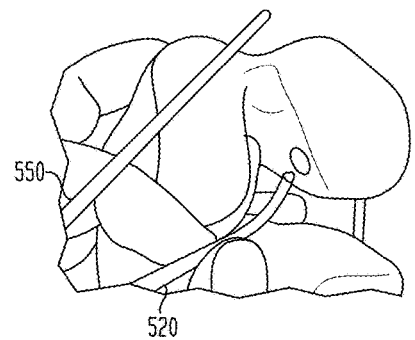
FIG. 26 illustrates an embodiment of a method of using an embodiment of a curved guide tool of the present invention on a knee joint.

In one embodiment of ACL repair using tool 510 (tool 610 may likewise be used, though for simplicity of illustration, tool 510 will be the exemplary instrument of this embodiment), an anterior-medial portal (not shown) is created in the tissue surrounding the knee joint, as is known in the art. A surgeon, as illustrated in FIGS. 24-26, for example, using the tool 510, holding the handle 515, may position the distal end 522 of the hollow curved guide 520 through the anterior-medial portal, and the distal tip 523 of the curved guide may be positioned on the femur surface. The distal tip 523 is pointed and may engage the femur to secure the distal end 522 at the desired position on the femur, in this case, the point of attachment of the ACL graft. Alternatively, distal tip 523 may be used as a starter awl to mark the desired attachment point. Once the desired attachment point is determined and the distal end 522 is secured to the femur, the outrigger 550 is swiveled away from the handle 515 and rotated towards the portion 521 of curved guide 520 and towards the outer skin surface of the patient (not shown). The outrigger 550 is swiveled until the extension 553 comes to rest on the outer skin surface of the patient, or into the surgical wound bed if the knee has been opened in that area or opened due to injury, for example. The ability of the outrigger to accurately designate the path of movement of the drill pin through the bone, while typically remaining on the outer surface of the skin, allows for a less invasive surgical procedure. This resting position may be at any point up to and including where the portion 521 of curved guide 520 is positioned within opening 552 of outrigger 550. It should also be understood that opening 552 prevents the outrigger main body 551 from contacting the portion 528 of curved guide 520.

Outrigger main body 551 may include a bend 555. Bend 555 may be applied to main body 551 for various reasons such as to provide a corner in which the surgeon may position a finger to easily swivel outrigger, or to allow outrigger 550 additional swivel movement towards curved guide 520 such that an angle between an axis of the curved guide, along its length, and an axis of the outrigger, along its length, is less than if the bend 555, and opening 552, were not present.

With outrigger 550 and distal tip 523 in place, a pin, or the like, may be passed up through the hollow curved guide 520 and passed into the femur using any known means, such as a power drill, mallet, or the like. The longitudinal axis of outrigger 553 may be generally within a plane of the handle 515 and curved guide 520. And, since outrigger is in the same plane as handle 515 and curved guide 520, the distal tip 523 of curved guide and the outrigger extension 553 should be in generally the same plane as well. As such, the outrigger extension 553 may provide a line of sight for the surgeon to orient himself as to where the pin will exit from the side of the femur and the surrounding skin. The line of sight allows the surgeon to locate the exiting portion of the pin quickly, and perform any necessary preparation of the surrounding skin prior to the pin passing through the skin and possibly creating unnecessary damage, such as excessive tearing of the skin, for example. The surgeon may direct the curved guide tool 510 into the joint at any angle, depending on the orientation of the handle 515 relative to the femur and tibia. Thus, the line of sight laid out by extension 553 may not be directly over the midline of the knee and femur but may instead be medial or lateral of this midline. Alternatively, it is recognized that if the tool 510 includes a movable screw rather than a setscrew 526, the surgeon may rotate the curved guide 520 around its axis, and the distal end 522 will thus curve to one side or the other of the plane, then the outrigger extension 553 and distal end 522 may not be in a single plane and the line of sight may be compromised. To alleviate this scenario, the outrigger 550 swivel connection 554 may instead be positioned on the portion 521 or 528 of curved guide such that outrigger 550 will remain in the same plane as the curved portion 522 of the curved guide 520.

Once the pin is passed through the femur and surrounding skin, the guide tool 510 may be removed from the surgical area. Alternative instrumentation, such as flexible reamer 30, 130, or the like, may then be used to widen the tunnel in the femur, prepare the tibia, and then the ACL graft may be placed and secured as is known in the art.

Figure 27:
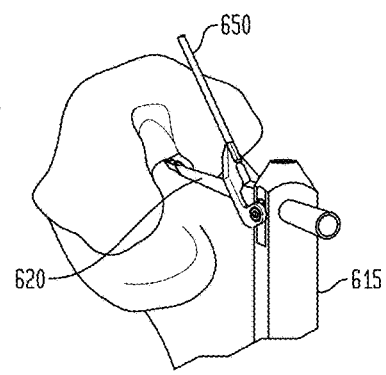
FIG. 27 illustrates a further embodiment of a method of using an embodiment of a curved guide tool of the present invention on a knee joint.
Figure 28:
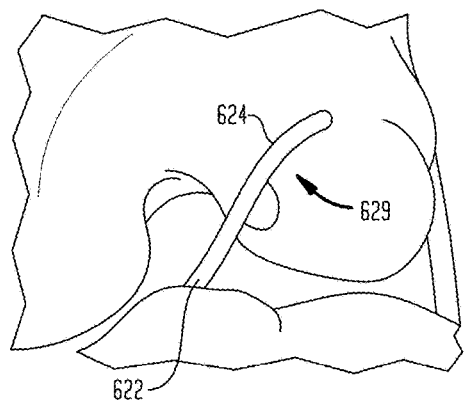
FIG. 28 illustrates one embodiment of a flange on a distal end of a curved guide adapted to substantially mimic the posterior portion of a lateral condyle used during surgery on a knee joint.
Figure 30:
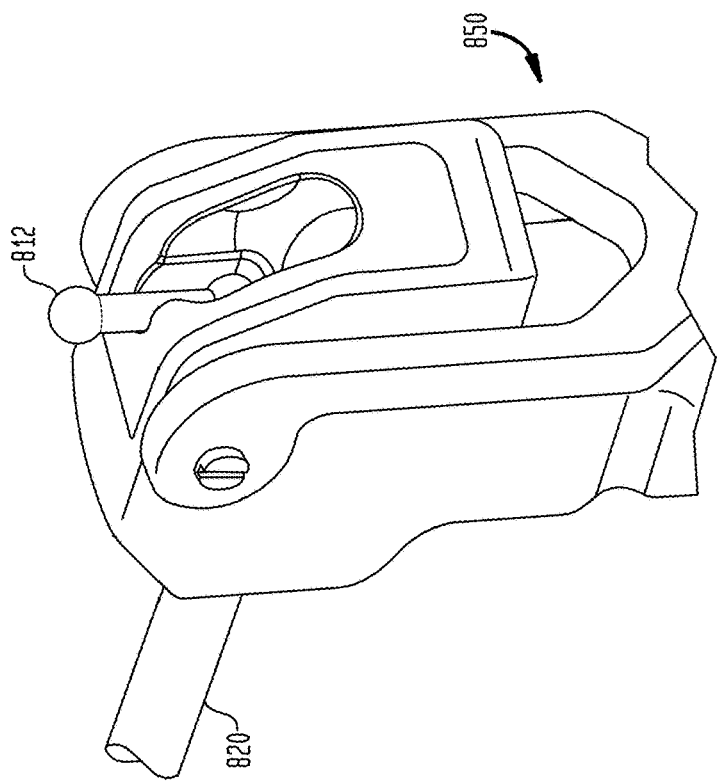
FIGS. 30 and 31 illustrate a close-up of a proximal end of the cannulated guide tool of FIG. 29.
Figure 29:
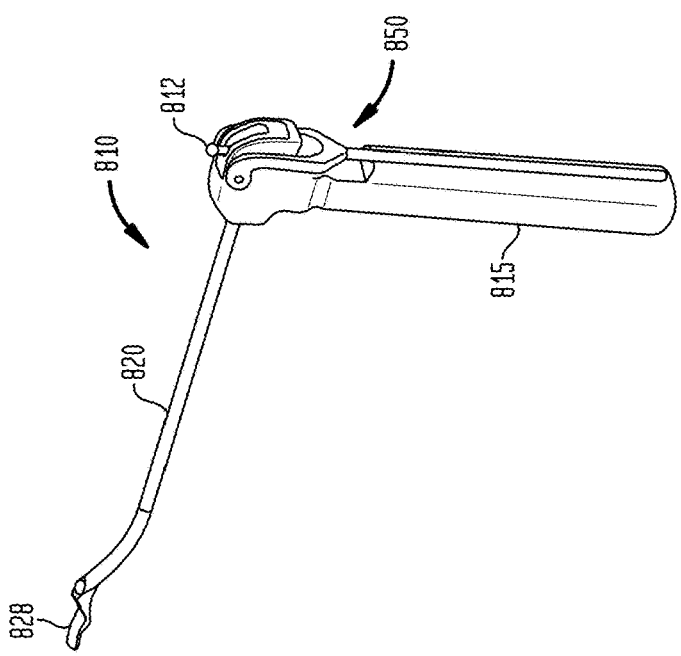
FIG. 29 illustrates a further embodiment of a cannulated guide tool of the present invention.

In an alternative embodiment of the above method, curved guide tool 610 may be used. The method is similar to the example discussed above with tool 510, except for the step of placement of the curved guide 620 onto the bone, such as the femur. Guide tool 610 may include flange 629, which is not intended to dig into bone. Rather, and as illustrated in FIGS. 27 and 28, flange 629 includes surface 624 which may be generally adapted to substantially mate with or index soft tissue or hard tissue near the surgical site, for example, a portion of a lateral condyle on the femur in the knee joint. For example, the surface 624 substantially mimics the surface of a portion of the lateral condyle such that it substantially mates with the condyle creating a stable connection which may alert the surgeon that the curved guide 620 is in a proper position. More particularly, for example, the flange 629 substantially mates with the posterior portion of the lateral condyle (FIG. 28). Of course, the shape of the flange 629 would vary depending on its use in a left knee or a right knee.

In yet a further embodiment, tool 510 and tool 610 may be used in conjunction with one another. For example, tool 510 may be first positioned into the joint, and the distal tip 523 used as an awl to mark the correct placement of the pin. For this embodiment, curved guide 520 of tool 510 may be solid, such that it is not hollow or cannulated. Tool 510 then may be removed from the joint, and tool 610 may then be inserted such that flange 629 positions on the surrounding tissue, e.g., distal portion of a lateral condyle on the femur, and once in proper position, and presumably aligned with the mark left by tool 510, a pin may be passed through curved guide 620 and into the femur. In a further alternative, only tool 610 would be used and a flexible starter awl may be passed through curved guide 620 to mark the correct anatomical position on the bone. The awl may then be removed and the pin passed into the curved guide 620 and into the femur.

Once the flange 629 is mated with the particular portion of the condyle its shape may substantially mimic, the distal portion 622 of curved guide 620 may be in the desired location to perform further steps, such as the passage of a pin, for eventual attachment of the soft tissue, such as an ACL graft, as discussed in other embodiments.

In yet another embodiment of ACL repair, using tool 810, a surgeon establishes a flow of clear liquid into the joint to increase visibility, using a fluid pump or the like (not shown). This step is inherent in any arthroscopic surgical procedure, including any of those described above. The surgeon next may create an anterior-medial portal (not shown) in the tissue surrounding the knee joint, as is known in the art. A surgeon, for example, using the tool 810, holding the handle 830, may position distal end 828 of the cannulated guide 820 through the anterior-medial portal, and into or adjacent to the joint. The plug 812 may be in the closed position during this insertion step, though it may be in the open position as well to, for example, release any air present in the cannulated opening. Once the tool 810 is in position, the plug may remain in the closed position until a time where the surgeon is ready to use tool 810.

With cannulated guide 820 in place, a flexible pin, or the like, may be passed up through the cannula entry and into the cannula guide 820 and passed into the femur using any known means, such as a power drill, mallet, or the like. Outrigger 850 may also be used to assist in guiding the pin into a proper position, as is discussed in detail above.

Once the pin is passed into the joint, the dam 814 may be closed again, or the guide tool 810 may be removed from the surgical area altogether. Alternative instrumentation, such as a flexible reamer or the like, may then be used to perform the surgical procedure.

The various instrumentation of the present invention may be grouped together in any any combination. Such instrumentation systems may include, for example, at least one flexible pin, at least one femoral aimer, at least one curved guide tool, and at least one flexible reamer. The system may further include at least one awl, suture, tissue graft preparation instruments, and any other instrumentation which may be used in arthroscopic surgical procedures. It should be noted that any of the below instrumentation system examples may include such instrumentation as suture, graft preparation instruments, and the like, as may be used in typical orthopedic arthroscopic surgical procedures.

In yet a further system, at least one of tool 510, tool 610 and tool 810, for at least a right or left knee, may be packaged with additional instrumentation needed for additional steps of, for example, ACL repair, such as at least one flexible drill pin 10, 110, 210, at least one femoral aimer 20, 120, 220, 320, 420, at least one femoral reamer 30, 130, or any other instrumentation known in the art.

Any other combination of the instrumentation of the present invention may also form a system. For example, at least one flexible pin and at least one flexible reamer may be combined as a system. Such a system may further include at least one femoral aimer, or alternatively, at least one curved guide tool. Such a system may further include at least one starter awl or at least one non-cannulated curved guide tool which may also operate as a starter awl.

In another combination, one instrumentation system may include at least one flexible pin and one of either an at least one femoral aimer or an at least one curved guide tool. Such a system may further include a flexible reamer, a starter awl, or the like.

A further exemplary instrumentation system may include a flexible reamer and one of either an at least one femoral aimer or an at least one curved guide tool. The system may further include a flexible pin, a starter awl, or the like.

Of course, an instrumentation system may also be combinable even where each instrument is packaged and arranged separately. For example, an instrumentation system including a flexible pin, flexible reamer, and at least one of a femoral aimer and a curved guide tool, may be packaged for a surgeon separately, meaning each instrument is sold separately and packaged individually. Alternatively, for example, each individual instrument may be available separately, and when a surgeon orders the instrumentation, the specific instrumentation ordered may be grouped together and packaged in a tray (not shown), which is then sterilized and sent to the surgeon. Thus, in this example, it is conceivable that every system of the present invention delivered to surgeons may be different from one another such that each system is tailored to fit the specific needs of the particular surgeon.

As yet another example, in one alternative of an instrumentation kit, it is envisioned that a curved guide tool may be part of a kit in which a tool 610 for a left knee and a tool 610 for a right knee are packaged together. Alternatively, a tool 610 could be packaged as a kit with detachable flanges 629, detachable at connection site 625, including at least one for the right knee and at least one for the left knee, or various flanges for a single knee but with various first and second offsets, or any combination of such. In yet a further alternative, at least two of tool 510, tool 610 and tool 810 may be packaged as a kit for either the left or right knee. Of course, an individual tool, for one of the right knee or left knee, could be packaged individually, or as a system in any combination of those discussed above.

A further kit may include various versions of a femoral aimer 20, 120, 220, 320, 420 with which a surgeon can determine which aimer best suits the particular characteristics of a surgical procedure. Such a kit may be specific to a left or a right knee. Alternatively, such a kit may include at least one femoral aimer for both a right and left knee. Of course, an individual aimer, for one of the right knee or left knee, could be packaged individually, or as a system in any combination of those discussed above.

These exemplary embodiments of various methods, instrumentation systems and kits may be used when the knee is positioned at a "normal" flexion, for example, at ninety degrees, and a knee holder (as is known in the art) may also be used, if needed. These methods reduce the need of a surgeon to hyperflex the knee, as well as providing methods of repairing an ACL in a knee that cannot undergo hyperflexion. However, the curvature of the drill pin 10, 110, 210, the curved guide 510, 610, 810 and consequently the reamer 30, 130 may vary such that the instrumentation, kits and methods of the present invention may be used on a knee, or other joint, bent at any degree of flexion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A guide tool for use in preparing a bone for soft tissue repair or reconstruction, comprising:
a guide having a linear proximal portion with a first end portion and a second end portion and a curved distal portion extending from the second end portion of the linear proximal portion to a distal tip, a longitudinal axis through the linear proximal portion defining a first axis, and a longitudinal axis through a distal end surface of the curved distal portion defining a second axis such that an angle between the first axis and the second axis is between zero degrees and ninety degrees, the distal end surface having a perimeter defined by an outer dimension of the guide such that the distal end surface faces away from the first axis;
a handle directly secured to the first end portion of the linear proximal portion of the guide;
an outrigger including an extension having a length extending from the first end portion of the linear proximal portion of the guide to a free end, the extension having a linear segment encompassing the free end constituting a majority of the length of the extension; and
a plane defined by the guide and outrigger such that the plane is positioned through a length of the guide and the length of the extension of the outrigger,
wherein the guide includes a guide path through the length of the guide and the guide path extends from the distal tip of the guide parallel to the second axis such that a portion of the guide path extending from the distal tip is unobstructed by the outrigger irrespective of a position of the outrigger on the guide tool.

2. The guide tool of claim 1, wherein the guide is cannulated and the cannulation defines the guide path for advancement of a drill pin or guide wire therethrough, the drill pin or guide wire extending distally from the distal tip of the guide unobstructed by the outrigger irrespective of a position of the outrigger on the guide tool.

3. The guide tool of claim 1, wherein the outrigger is movable relative to the handle and the guide.

4. The guide tool of claim 3, wherein the outrigger is adapted to be moved to contact outer tissue outside of a surgical site and along the plane.

5. The guide tool of claim 1, wherein the extension includes a longitudinal axis along its length, the outrigger adapted to provide a line of sight along the plane.

6. The guide tool of claim 1, wherein the guide includes a flange secured adjacent the distal tip of the guide, the flange extending from the distal tip and offset from the first axis of the guide, the flange having a shape defined by a first curve extending in at least a first direction along at least a portion of the flange and a degree of tilt, relative to the plane, along at least a second portion of the flange wherein the second portion overlaps with the first portion.

7. The guide tool of claim 1, wherein the second end portion of the linear proximal portion includes an end that separates the linear proximal portion and the curved distal portion, and the linear proximal portion and the curved distal portion extend in opposite directions from the end.

8. An instrument for use in preparing a bone for soft tissue repair or reconstruction, comprising:
a guide tool including a guide, the guide having a length extending between a first end and a second end, wherein the guide includes a linear portion adjacent to the first end that defines a first longitudinal axis and a curved portion adjacent to the second end, a longitudinal axis through the guide at the second end defining a second longitudinal axis, the first longitudinal axis at an angle relative to the second longitudinal axis and the curved portion continuous with the remainder of the guide such that the guide is integral, a handle secured to the guide adjacent to the first end, and an outrigger movably mounted on the guide adjacent to the first end, the outrigger including an extension defining a third longitudinal axis, the extension positionable relative to the bone such that a line of sight established by the third longitudinal axis designates an exit point from the bone along the second longitudinal axis, wherein, with the guide tool in position to prepare the bone, a guide path extending from the second end of the guide coincident to the second longitudinal axis, and passing through the exit point, is unobstructed by the outrigger irrespective of a position of the outrigger on the guide tool, wherein the angle is between zero degrees and ninety degrees, wherein the guide path represents a path of travel for an object placed through the guide, and wherein the extension has a length extending from a connection to the guide tool to a free end, a continuous segment of the extension measured from the free end being linear and constituting a majority of the length of the extension.

9. The instrument of claim 8, wherein the guide is cannulated and the cannulation defines a portion of the guide path for advancement of a drill pin or guide wire therethrough, the drill pin or guide wire extending distally from the second end of the guide unobstructed by the outrigger irrespective of a position of the outrigger on the guide tool.

10. The instrument of claim 8, wherein the outrigger is adapted to contact outer tissue outside of a reattachment site along a plane defined by the guide and the outrigger such that the plane is positioned through the guide and outrigger.

11. The instrument of claim 8, wherein the linear portion and the curved portion abut one another at a first location on the length of the guide and the linear portion and the curved portion extend in opposite directions from the first location.

12. An instrumentation system for preparing a bone for soft tissue repair, the instrumentation system comprising:
a flexible drill pin capable of bending along a curved path;
a cannulated curved guide tool having a curved guide, the curved guide having a length extending between a first end and a second end with a cannulated linear portion adjacent to the first end and a cannulated curved portion adjacent to the second end such that the cannulated linear portion defines a first longitudinal axis and the cannulated curved guide at the second end defines a second longitudinal axis, the first longitudinal axis at an angle relative to a second longitudinal axis and the curved portion continuous with the remainder of the guide such that the curved guide is integral, a handle secured to the curved guide adjacent to the first end, and an outrigger including an extension extending from the curved guide and connected to the curved guide adjacent to the first end, the outrigger defining a third longitudinal axis, wherein the angle is between zero degrees and ninety degrees, wherein the cannulation defines a guide path through the cannulated curved guide tool and the guide path is linear through the cannulated linear portion and nonlinear through the cannulated curved portion, wherein the cannulated curved guide tool is adapted to accept the flexible drill pin such that the flexible drill pin passes through the first and second ends of the curved guide and extends from the second end along the second longitudinal axis into a reattachment site, passes through the bone, and protrudes through skin at an exit point, wherein the third longitudinal axis of the outrigger is adapted to establish a line of sight to the exit point, and wherein the flexible drill pin is unobstructed by the outrigger between the second end of the guide and the exit point irrespective of a position of the outrigger on the guide tool.

13. The instrumentation system of claim 12, wherein the outrigger is movable relative to the handle and the curved guide.

14. The instrumentation system of claim 13, wherein the outrigger is adapted to contact outer tissue outside of the reattachment site along a plane defined by the curved guide and the outrigger such that the plane is positioned through the curved guide and outrigger.

15. The instrumentation system of claim 12, wherein the outrigger includes a body with an opening therein.

16. The instrumentation system of claim 15, wherein the outrigger is moved such that a portion of the curved guide proximal to the first end is positioned within the opening of the outrigger.

17. The instrumentation system of claim 12, wherein the flexible drill pin includes a length extending to a distal end having a trocar tip and a neck positioned along a portion of the length of the flexible drill pin adjacent to the distal end.

18. A method of preparing a bone for reattachment of soft tissue thereto, comprising:
obtaining a guide tool as recited in claim 1;
positioning the distal tip of the guide tool at a reattachment site;
positioning the outrigger relative to a bone such that a line of sight through the outrigger designates an exit point of a flexible drill pin; and
inserting the flexible drill pin through a cannulated body of the guide and into the bone at the reattachment site, wherein the flexible drill pin projects into the reattachment site, passes through the bone, and protrudes through skin at the exit point along the line of sight,
wherein the inserted flexible drill pin is unobstructed by the outrigger irrespective of a position of the outrigger on the guide tool.

19. The method of claim 18, wherein the guide tool is selected from a plurality of cannulated curved guide tools.

20. The method of claim 19, further comprising the step of visualizing the reattachment site.

21. The method of claim 18, further comprising the step of adjusting the positioning of the guide tool and the outrigger to move the line of sight to revise the location of the exit point.

* * * * *